(12) United States Patent
Finnestad et al.

(10) Patent No.: US 8,201,704 B2
(45) Date of Patent: *Jun. 19, 2012

(54) MEDICAL WASTE DISPOSAL SYSTEM

(76) Inventors: Brian Finnestad, Huntley, IL (US);
John Japuntich, Harvard, IL (US);
Robert Joseph Panek, Jr., Huntley, IL (US); Anton M. Smudde, Elk Grove Village, IL (US)

( * ) Notice: Subject to any disclaimer, the term of this patent is extended or adjusted under 35 U.S.C. 154(b) by 1464 days.

This patent is subject to a terminal disclaimer.

(21) Appl. No.: 11/085,488

(22) Filed: Mar. 21, 2005

(65) Prior Publication Data
US 2005/0218142 A1 Oct. 6, 2005

Related U.S. Application Data

(63) Continuation-in-part of application No. 09/845,976, filed on Apr. 30, 2001, now Pat. No. 7,114,629.

(51) Int. Cl.
*B65F 1/08* (2006.01)
(52) U.S. Cl. ............... 220/23.86; 220/23.87; 220/23.91; 220/262; 220/264; 220/908
(58) Field of Classification Search .................. 220/908, 220/263, 264, 262, 345.4, 345.2, 348, 23.91, 220/908.1
See application file for complete search history.

(56) References Cited

U.S. PATENT DOCUMENTS

| | | | |
|---|---|---|---|
| 1,315,143 A | 9/1919 | Masters | |
| 2,351,597 A | 5/1942 | Burlin | |
| 2,667,320 A | 11/1952 | Whitley | |
| 2,634,933 A | 4/1953 | Grimsley | |
| 3,008,604 A | 11/1961 | Garner | |
| 3,041,030 A | 6/1962 | Heimrich | |
| 3,064,931 A | 11/1962 | Rowe | |
| 3,208,706 A | 9/1965 | Clark | |
| 3,333,721 A | 8/1967 | Marek | |
| 3,347,507 A | 10/1967 | Dyer | |
| 3,514,007 A | 5/1970 | Woods, Sr. | |
| 3,869,979 A | 3/1975 | Sulcek | |
| 4,280,640 A | 7/1981 | Daloisio | |
| 4,338,987 A | 7/1982 | Miles | |
| 4,420,168 A | 12/1983 | Dewing | |
| 4,637,545 A | 1/1987 | Stewart | |
| 4,765,548 A | 8/1988 | Sing | |

(Continued)

FOREIGN PATENT DOCUMENTS

DE 890623 9/1953

OTHER PUBLICATIONS

SHARPSAFETY Brochure of Tyco Healthcare, dated Dec. 2000.

(Continued)

*Primary Examiner* — Stephen Castellano
(74) *Attorney, Agent, or Firm* — Lisa E. Winsor, Esq.

(57) ABSTRACT

A container system is provided with a container having a door mounted for pivotal reciprocation about a door pivot axis between opened and closed positions. The container system also has a carrier with a body receiving the container and an arm coupled to the body for pivotal reciprocation about an arm pivot axis that is oriented substantially parallel to the door pivot axis. The arm engages the door of the container, and the pivotal reciprocation of the arm reciprocates the door of the container between the opened and closed positions.

30 Claims, 27 Drawing Sheets

U.S. PATENT DOCUMENTS

| | | | |
|---|---|---|---|
| 4,768,742 A | 9/1988 | Kaaloa |
| 4,883,189 A | 11/1989 | Löbbert |
| 4,911,294 A | 3/1990 | Russo et al. |
| 4,913,309 A | 4/1990 | Fink |
| 4,949,866 A | 8/1990 | Sanders |
| 5,048,712 A | 9/1991 | Wolters |
| 5,082,132 A | 1/1992 | Tsai |
| 5,107,990 A | 4/1992 | Wicherski et al. |
| D326,753 S | 6/1992 | DeBusk |
| 5,143,389 A | 9/1992 | Jonkers |
| 5,163,574 A | 11/1992 | Sosan |
| D332,852 S | 1/1993 | Delmerico |
| 5,195,649 A | 3/1993 | Wolters |
| 5,230,525 A | 7/1993 | Delmerico et al. |
| 5,235,795 A | 8/1993 | DeBusk |
| D341,237 S | 11/1993 | DeBusk |
| 5,348,222 A | 9/1994 | Patey |
| 5,354,023 A | 10/1994 | Meeks |
| D352,350 S | 11/1994 | Rambo et al. |
| 5,372,271 A | 12/1994 | Miller et al. |
| D358,240 S | 5/1995 | Mosior |
| 5,415,315 A | 5/1995 | Ramirez |
| 5,419,435 A | 5/1995 | Perzan et al. |
| 5,474,201 A | 12/1995 | Liu |
| 5,531,346 A | 7/1996 | Mosior |
| 5,531,348 A | 7/1996 | Baker et al. |
| 5,538,158 A | 7/1996 | Prout et al. |
| 5,570,547 A | 11/1996 | Webb et al. |
| 5,582,322 A | 12/1996 | Prout et al. |
| 5,590,840 A | 1/1997 | Adams et al. |
| 5,641,171 A | 6/1997 | Posey et al. |
| 5,659,247 A | 8/1997 | Clements |
| 5,671,859 A | 9/1997 | Sheu et al. |
| 5,673,811 A | 10/1997 | Dickinson et al. |
| D388,577 S | 12/1997 | Rehrig et al. |
| 5,730,451 A | 3/1998 | Walker |
| D393,334 S | 4/1998 | Presnell et al. |
| 5,779,047 A | 7/1998 | Darrah |
| 5,881,896 A | 3/1999 | Presnell et al. |
| 5,899,468 A | 5/1999 | Apps et al. |
| 5,947,285 A | 9/1999 | Gaba et al. |
| 6,010,024 A | 1/2000 | Wang |
| 6,053,354 A | 4/2000 | Niemeyer |
| 6,138,558 A | 10/2000 | Harrington |
| 6,202,922 B1 | 3/2001 | Phillips et al. |
| D445,228 S | 7/2001 | Apps et al. |
| D478,701 S | 8/2003 | Panek, Jr. |
| 6,623,316 B1 | 9/2003 | Wu |
| 6,626,316 B2 | 9/2003 | Yang |
| 6,626,321 B2 | 9/2003 | Jaeger |
| 6,651,992 B1 | 11/2003 | Smith, Sr. |
| 6,722,672 B2 | 4/2004 | Cates et al. |
| 7,114,629 B2 * | 10/2006 | Panek, Jr. | 220/345.1 |
| 7,364,049 B2 * | 4/2008 | Panek, Jr. | 220/345.1 |
| 2002/0158068 A1 | 10/2002 | Panek, Jr. |
| 2004/0020927 A1 | 2/2004 | Yang et al. |

OTHER PUBLICATIONS

General translation of Office Action of Mexican Patent Office.
Office action issued May 1, 2009 in related U.S. Appl. No. 12/047,784. 8 pgs.
Response filed Sep. 1, 2009 to Office Action dated May 1, 2009 from related U.S. Appl. No. 12/047,784. 12 pgs.
Office action issued Dec. 2, 2009 in related U.S. Appl. No. 12/047,784. 9 pgs.
Response filed Apr. 1, 2010 to Office Action dated Dec. 2, 2009 from related U.S. Appl. No. 12/047,784. 13 pgs.
Office action issued Jul. 21, 2010 in related U.S. Appl. No. 12/388,085. 12 pgs.
Response filed Nov. 22, 2010 to Office Action dated Jul. 21, 2010 from related U.S. Appl. No. 12/388,085. 26 pgs.
Office action issued Feb. 25, 2011 in related U.S. Appl. No. 12/388,085. 9 pgs.
Response filed Mar. 24, 2011 to Office Action dated Feb. 25, 2011 from related U.S. Appl. No. 12/388,085. 11 pgs.
Office action issued Sep. 13, 2011 in related U.S. Appl. No. 09/845,976. 8 pgs.
Response filed Jan. 14, 2002 to Office Action dated Sep. 13, 2001 from related U.S. Appl. No. 09/845,976. 11 pgs.
Office action issued Apr. 17, 2002 in related U.S. Appl. No. 09/845,976. 8 pgs.
Response filed Aug. 19, 2002 to Office Action dated Apr. 17, 2002 from related U.S. Appl. No. 09/845,976. 8 pgs.
Office action issued Nov. 18, 2002 in related U.S. Appl. No. 09/845,976. 7 pgs.
Response filed May 14, 2003 to Office Action dated Nov. 18, 2002 from related U.S. Appl. No. 09/845,976. 22 pgs.
Office action issued Jul. 17, 2003 in related U.S. Appl. No. 09/845,976. 10 pgs.
Response filed Jan. 16, 2004 to Office Action dated Jul. 17, 2003 from related U.S. Appl. No. 09/845,976. 31 pgs.
Office action issued Apr. 7, 2004 in related U.S. Appl. No. 09/845,976. 6 pgs.
Response filed Oct. 6, 2004 to Office Action dated Apr. 7, 2004 from related U.S. Appl. No. 09/845,976. 28 pgs.
Office action issued Aug. 4, 2005 in related U.S. Appl. No. 09/845,976. 5 pgs.
Response filed Feb. 3, 2006 to Office Action dated Aug. 4, 2005 from related U.S. Appl. No. 09/845,976. 8 pgs.
Office action issued Jul. 5, 2006 in related U.S. Appl. No. 10/792,361. 8 pgs.
Response filed Jan. 3, 2007 to Office Action dated Jul. 5, 2006 from related U.S. Appl. No. 10/792,361. 16 pgs.
Office action issued Feb. 20, 2007 in related U.S. Appl. No. 10/792,361. 6 pgs.
Response filed May 17, 2007 to Office Action dated Feb. 20, 2007 from related U.S. Appl. No. 10/792,361. 6 pgs.
Office action issued Jun. 8, 2009 in related U.S. Appl. No. 12/047,766. 11 pgs.
Response filed Sep. 8, 2009 to Office Action dated Jun. 8, 2009 from related U.S. Appl. No. 12/047,766. 25 pgs.
Office action issued Jan. 5, 2010 in related U.S. Appl. No. 12/047,766. 13 pgs.
Office action issued Aug. 6, 2009 in related U.S. Appl. No. 12/047,828. 9 pgs.
Response filed Nov. 6, 2009 to Office Action dated Aug. 6, 2009 from related U.S. Appl. No. 12/047,828. 12 pgs.

* cited by examiner

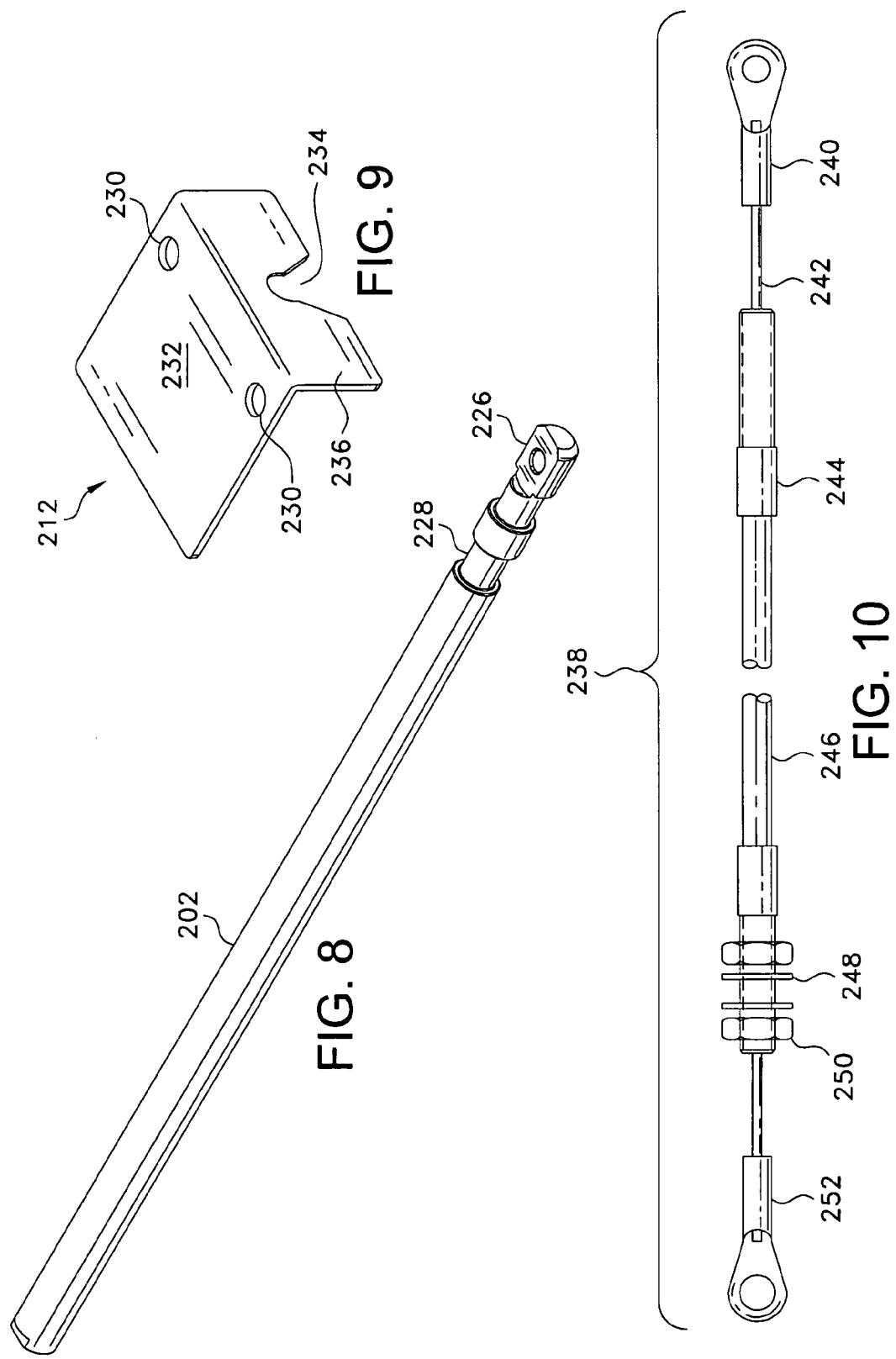

MEDICAL WASTE DISPOSAL SYSTEM

CROSS REFERENCE TO RELATED APPLICATIONS

This application is a continuation-in-part of U.S. application Ser. No. 09/845,976, filed Apr. 30, 2001, now U.S. Pat. No. 7,114,629.

BACKGROUND OF THE INVENTION

This invention relates generally to the disposal of contaminated items and, in particular, to a system for use in a hospital or a similar environment where contaminated items are to be collected and disposed of without creating a hazard for patients or hospital personnel.

In hospitals, clinics and similar medical institutions, contamination continues to be of utmost concern. The prevention of the spread of communicable diseases is a major priority; therefore, disposable, single-use, patient care products have become prevalent.

Such patient care products are contaminated, once used, and can transmit disease. These patient care products include devices such as hypodermic needles, intravenous needles, lasers, scalpel blades or other sharps—all of which are required to be disposed at their point of usage under current guidelines of the United States Centers for Disease Control.

Various disposal containers for medical waste have been proposed for the purpose of preventing individuals from gaining access to contaminated items, such as sharps, once the waste has been deposited into the container. For example, a waste container having a top with a slidable closure is disclosed by Mosior in U.S. Pat. No. 5,531,346. The top of the waste container disclosed by Mosior has an access aperture, and the slidable closure on the top is positioned to slide between opened and closed positions. The closure includes a handle to facilitate sliding movement of the closure. The closure disclosed by Mosior can be temporarily retained in a first closed position over the aperture, and can be permanently retained in a second closed position over the aperture.

A protective container is disclosed by Marek in U.S. Pat. No. 3,333,721. A removable cover of the container disclosed by Marek is interlockable with panels of the container, and the removable cover has a door opening and a slidable door positioned under the cover. The door of the container disclosed by Marek is moved by means of a cable that passes through the cover and is fastened at its lower end to a foot-pedal.

Despite these proposed containers, there remains a need, however, for an improved medical waste disposal system that can further reduce the chance of contact between the medical personnel and the medical waste and to help prevent unauthorized access to medical waste held within the container.

SUMMARY OF THE INVENTION

According to one aspect of the invention, a container system is provided with a container having a door mounted for pivotal reciprocation about a door pivot axis between opened and closed positions. The container system also has a carrier with a body receiving the container and an arm coupled to the body for pivotal reciprocation about an arm pivot axis that is oriented substantially parallel to the door pivot axis. The arm engages the door of the container, and the pivotal reciprocation of the arm reciprocates the door of the container between the opened and closed positions.

According to another aspect of the invention, a carrier is provided having a body portion at least partially defining a cavity receiving a container, an upper portion coupled to the body portion and extending over at least a portion of the container, and an arm coupled to the upper portion for pivotal movement with respect to the upper portion.

According to yet another aspect of the invention, a container system is provided with a carrier having a body portion and an arm coupled for reciprocal movement with respect to the body portion, the arm having a first portion coupled to the body portion and a second portion pivotally coupled to the first portion and engaging a surface of the door.

According to still another aspect of the invention, a container system is provided with a carrier having a body with a wall portion that is substantially hollow. An arm is coupled for reciprocal movement with respect to the body portion, and a flexible member is coupled to the arm to facilitate reciprocal movement of the arm. The flexible member extends through the substantially hollow wall portion of the body.

BRIEF DESCRIPTION OF THE DRAWING

The invention is best understood from the following detailed description when read in connection with the accompanying drawing. It is emphasized, according to common practice, that various features illustrated in the drawing are not to scale. On the contrary, the dimensions of the various features are arbitrarily expanded or reduced for clarity. Included in the drawing are the following figures:

FIG. 8 is a perspective view of an embodiment of an extension or arm component of the arm control assembly illustrated in FIG. 7.

FIG. 9 is a perspective view of a locking member component of the arm control assembly illustrated in FIG. 7.

FIG. 10 is a plan view of an embodiment of a cable assembly adapted for use in the container system illustrated in FIG. 1.

DETAILED DESCRIPTION OF THE INVENTION

Figure 1:
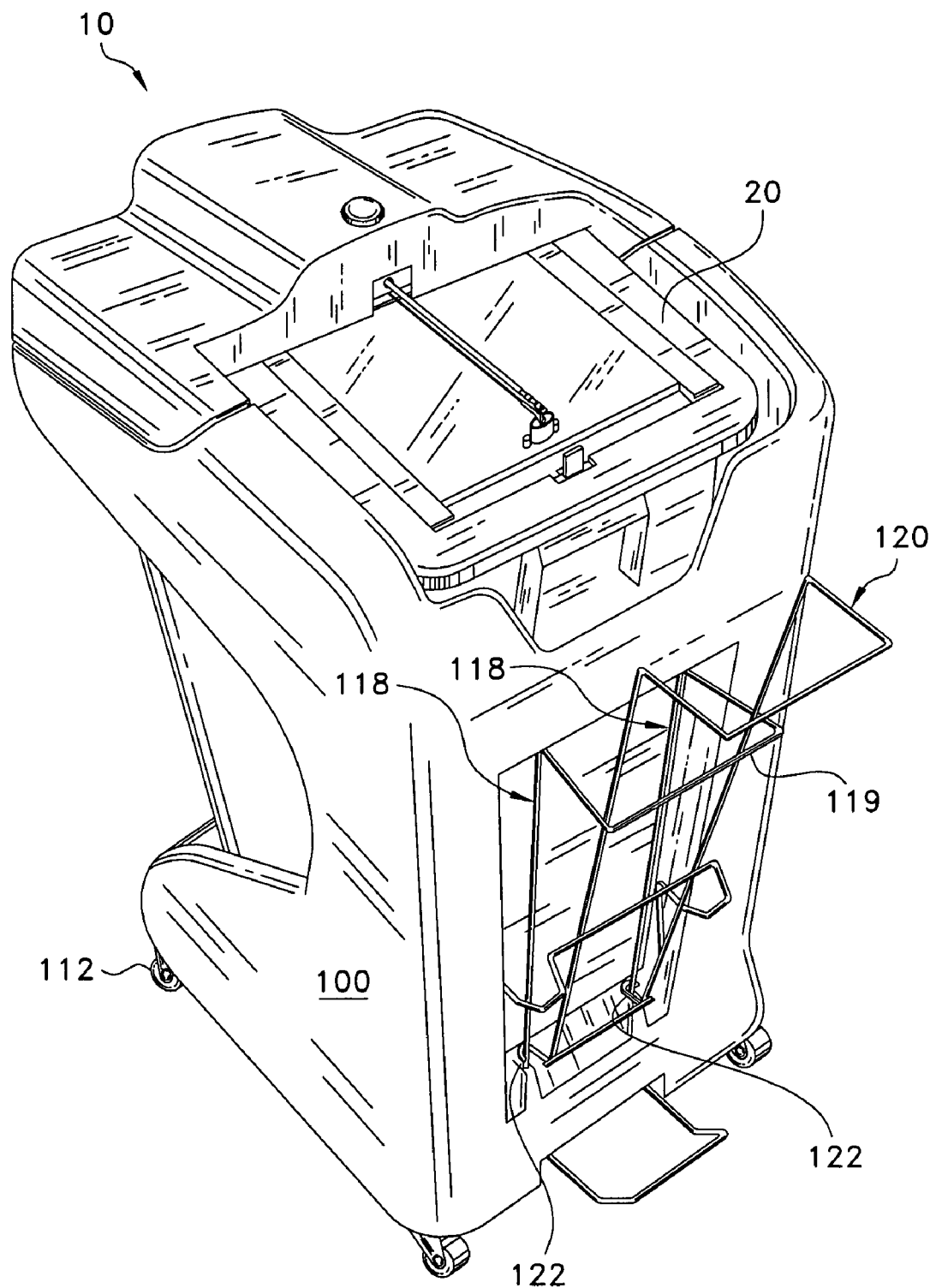
FIG. 1 is a perspective view of an embodiment of a container system according to this invention.

Exemplary details of this invention will now be described with reference to preferred embodiments selected for illustration in the Figures. It will be appreciated that the Figures have not been rendered to any particular scale or proportion. Also, it will be appreciated that the scope of this invention is not limited to the embodiments selected for illustration in the Figures. Instead, the scope of this invention is defined separately in the appended claims.

Generally, referring to the Figures, this invention provides a carrier 100 that is configured to hold a medical waste container 20 having a door 26 mounted for reciprocation between opened and closed positions. The carrier 100 includes a body 105 that is adapted to receive the medical waste container 20. The carrier 100 also includes an extension or arm 202 coupled for reciprocal movement with respect to the body 105. The arm 202 is adapted for engagement with the door 26 of the medical waste container 20. The reciprocal movement of the arm 202 is adapted to reciprocate the door 26 of the medical waste container 20 between the opened and closed positions.

This invention also provides a container system 10 including the medical waste container 20 in combination with the carrier 100. The system 10 has been discovered to reduce contact between medical professionals and the medical waste container 20 during use. The system 10 has also been discovered to resist unauthorized use of, and unintended access to the interior of, the medical waste container 20.

Referring specifically to FIG. 1, the medical waste container system 10 includes a carrier 100 that can receive the medical waste container 20. The carrier 100 includes several features to facilitate the mobility of the medical waste container system 10. Specifically, the carrier 100 includes four (4) wheels 112 mounted at the base of the carrier 100 so that the medical waste container system 10 can easily and readily be transported from one position to another by a user of the system 10. Two (2) of the four (4) wheels 112 are preferably lockable so that movement of the system 10 along the ground can be prevented or controlled.

Also, an extendable handle 120 extends upwardly and outwardly from the carrier 100 so that the container system 10 can be pulled by a user. More specifically, the handle 120 is formed from thick metallic wire formed into an elongated loop that terminates at its base with a pair of loops 122. Those loops 122 engage a pair of vertically-extending handle guides 118 which are fixed to the body of the carrier 100. A loop 119 extends between the handle guides 118 toward the top portion of the handle guides 118, thereby forming a support against which the upper portion of the handle 120 rests.

It will be understood that the handle 120 can be extended upwardly and outwardly with respect to the carrier 100 by virtue of the sliding relationship between the loops 122 at the base of the handle 120 and the handle guides 118 to which the loops 122 are slidingly engaged. As the handle loops 122 slide upwardly along the handle guides 118, the handle 120 extends upwardly and outwardly with respect to the carrier 100, while still resting against the loop 119 toward the top of the handle guides 118. When in this extended position, a user of the system 10 can easily move the carrier 100 from one location to another. When finished, the user can release the handle 120 to the retracted position as the loops 122 at the base of the handle 120 slide downwardly along the handle guides 118.

Figure 2:
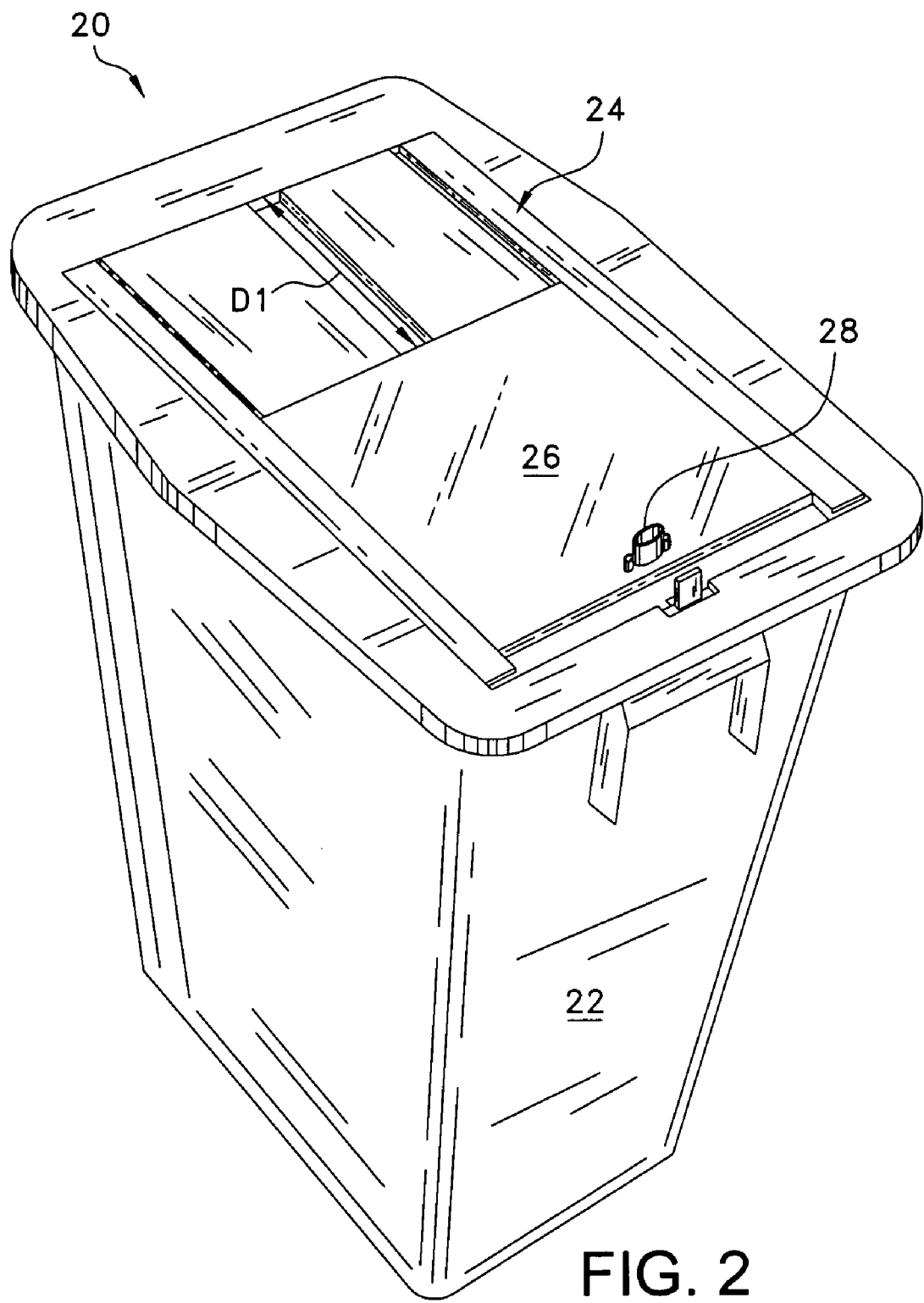
FIG. 2 is a perspective view of a container than can be used as a component of the container system illustrated in FIG. 1.

Referring now to FIG. 2, a preferred embodiment of a medical waste container 20 is illustrated, which container can be used in the medical waste container system 10 illustrated in FIG. 1. An exemplary waste container is disclosed by Mosior in U.S. Pat. No. 5,531,346, which is incorporated herein by reference. An exemplary waste container is also available from Tyco Healthcare Group LP of Mansfield, Mass. (see, e.g., Product Nos. 8938, 8998S, 8935, 8936SA, 8939 and 8934).

The medical waste container 20 includes a receptacle 22 on which a lid 24 is engaged. A door 26 is mounted for sliding reciprocation with respect to the lid 24. More specifically, the door 26 slides with respect to the lid 24 in the direction indicated by the arrow labeled D1. In FIG. 2, the door 26 is shown in the closed position. As the door 26 slides in the direction D1, the door 26 moves from the closed position (as illustrated) to an opened position (not shown in FIG. 1). When the door 26 is in the closed position, access to the interior of the medical waste container 20 is prevented. Conversely, when the door 26 is in the opened position, access is provided to the interior of the receptacle 22 so that medical waste can be inserted for disposal.

It will be understood that the medical waste container system 10 illustrated in FIG. 1, helps to reduce contact between the user of the system 10 and the medical waste container 20. More specifically, as will be described later in further detail, is no longer necessary for the user of the system 10 to make hand contact with the door 26 of the medical waste container 20 in order to open the container 20 and gain access to the interior of the receptacle 22 (in order to discard medical waste) or to close the door 26 to prevent such access. Also, the medical waste container system 10 makes it possible to prevent unauthorized or inadvertent access to the interior of the medical waste container 20, as will be described later in further detail.

Figure 3:
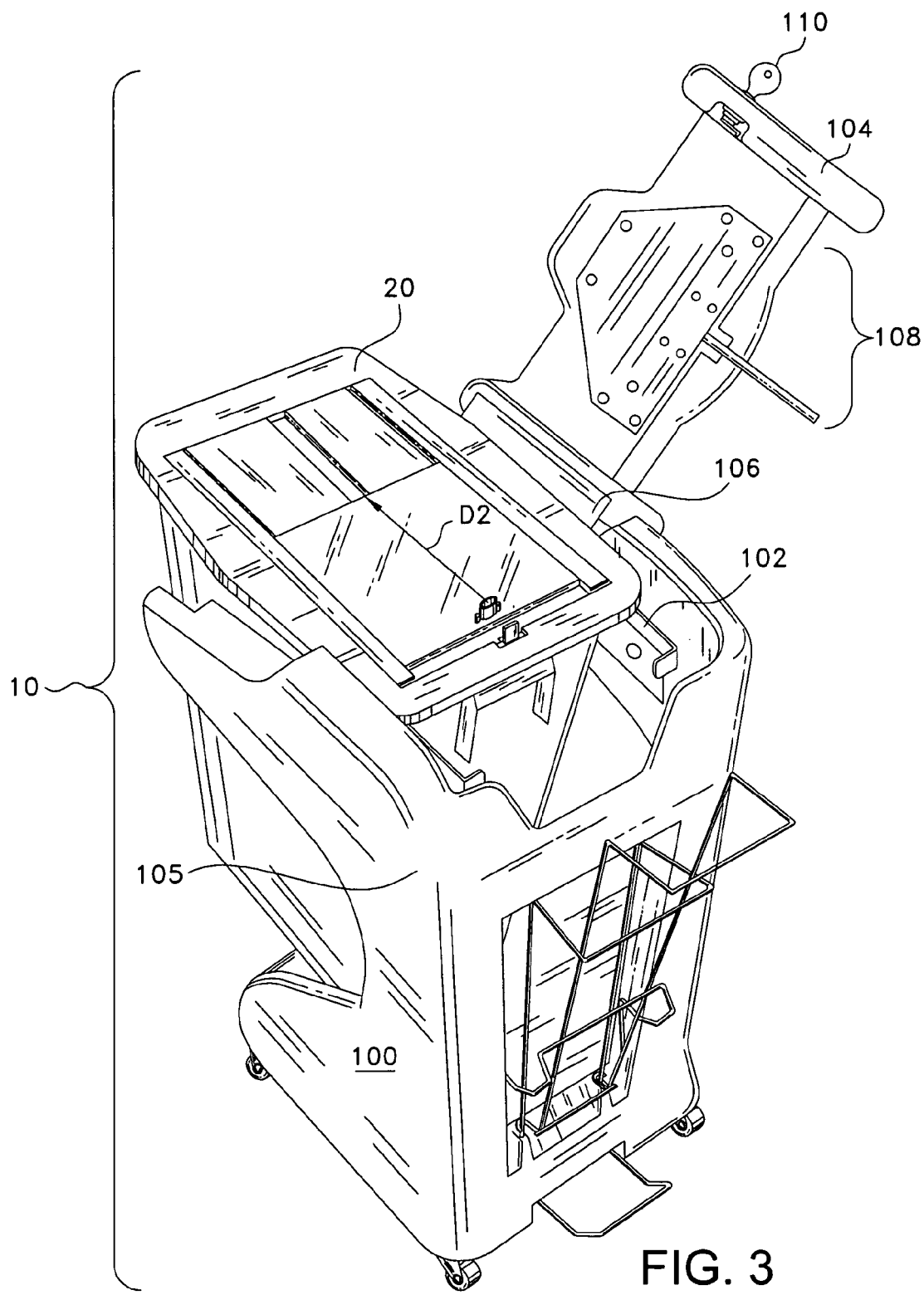
FIG. 3 is a perspective view of the container system illustrated in FIG. 1, as the container illustrated in FIG. 2 is being inserted into or withdrawn from a carrier component of the container system illustrated in FIG. 1.

Referring now to FIG. 3, the removal of the medical waste container 20 from the carrier 100 is illustrated. A body component 105 of the carrier 100 includes a pair of opposed guide rails 102 (only one shown in FIG. 3) in order to support the medical waste container 20 when it is positioned within the interior defined by the carrier 100. More specifically, the guide rails 102 provide a pair of supports against which the lip of the receptacle 22 and/or skirt of the lid 24 can rest. The container 20 can therefore be suspended and/or supported by the carrier 100.

The carrier 100 also includes a hood component 104 that is coupled by means of a hinge 106 to the body 105 of the carrier 100. The hinge 106 makes it possible to rotate the hood 104 with respect to the body 105 so that the hood 104 can be moved between an opened position (as shown in FIG. 3) and a closed position (as shown in FIG. 1) The view provided in FIG. 3 also reveals a door retractor assembly 108, which is used to open and close the door 26 of the medical waste container 20, as will be described in further detail later.

When the hood 104 is rotated by means of the hinge 106 into a closed position (as shown in FIG. 1), removal of the medical waste container 20 from the carrier 100 is prevented. Also, a lock 110 is preferably provided on the hood 104 in order to lock the hood 104 in a closed position with respect to the body 105 of the carrier 100. Lock 110 can be a simple key lock, wherein rotation of the key brings about (or releases) engagement between the hood 104 and the body 105.

When the medical waste container 20 is desired to be removed from the carrier 100 (e.g., when the container 20 is filled with medical waste), it can be removed from the carrier 100 by unlocking the lock 110 on the hood 104, rotating the hood 104 from the closed position shown in FIG. 1 to the opened position shown in FIG. 3 by virtue of the hinge 106, and removing the medical waste container 20 from the carrier 100 in the direction designated by the arrow D2 in FIG. 3. The removal procedure can be reversed in order to introduce the medical waste container 20, or a replacement container 20, into the interior defined by the carrier 100.

The body 105 of the carrier 100 includes a pair of detents 113 that are positioned to mate with a corresponding pair of recesses 115 in the hood 104. The mating engagement of detents 113 and recesses 115 provides for alignment between the hood 104 and the body 105 when the 104 is being closed.

Figure 4:
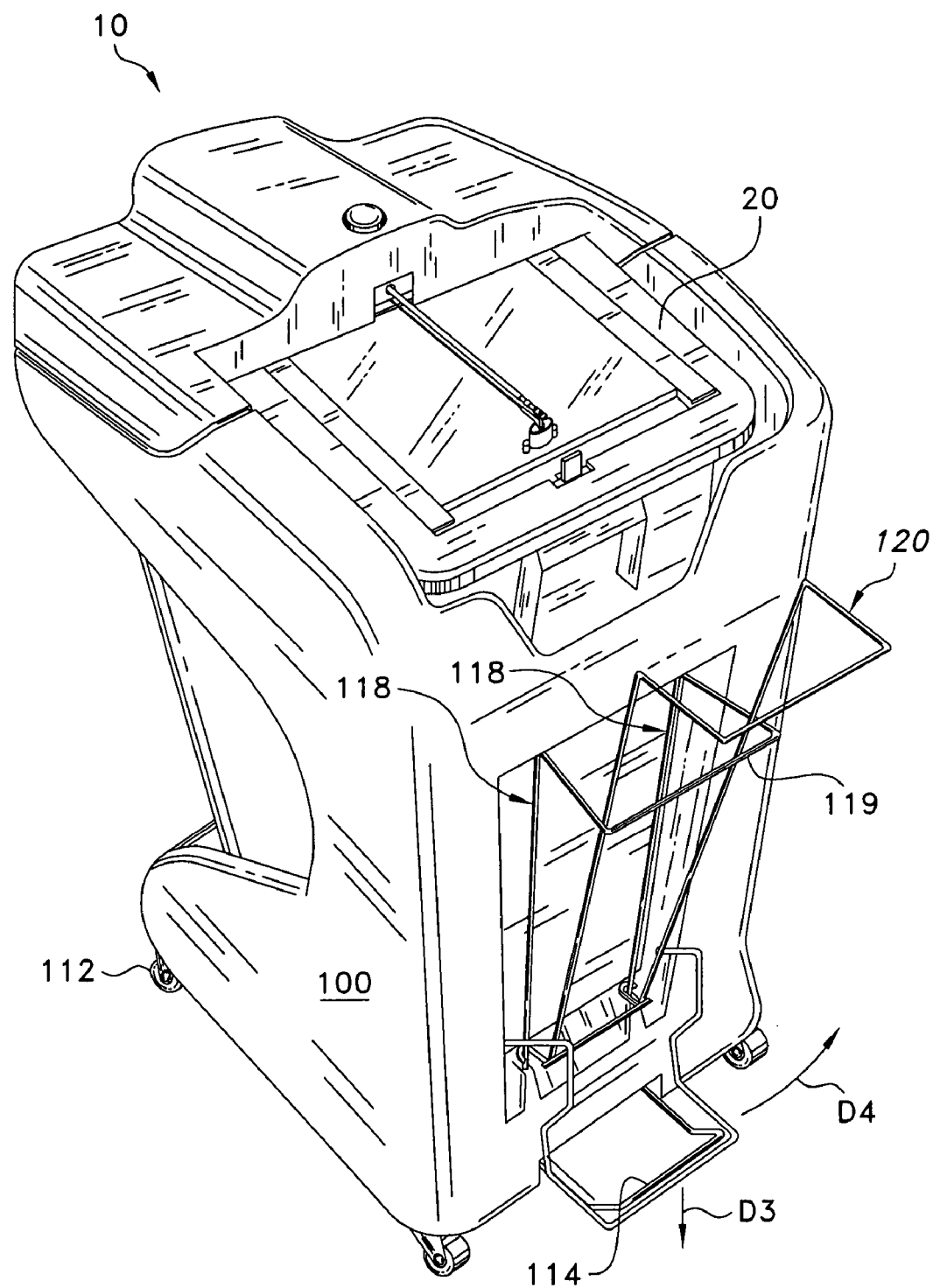
FIG. 4 is a perspective view of a base portion of the container system illustrated in FIG. 1.

Referring now to FIG. 4, a lower portion of the medical waste container system 10 is illustrated. The carrier 100 of the system 10 includes a lever 114, such as a foot pedal for example, in order to open and close the door 26 of the medical waste container 20. More specifically, the lever 114 is depressed downwardly by the foot of a user in the direction designated in FIG. 4 by the arrow D3. As will be described later in further detail, a cable coupled to the lever 114 runs from the lever, extends through the interior of the hollow body 105 of the carrier 100, and is coupled to a mechanism (arm control assembly 200 shown in FIG. 7) for opening and closing the door 26 of the medical waste container 20.

Although the foot pedal version of lever 114 shown in FIG. 4 can be replaced by a hand operated lever, the preferred operation of the lever 114 by the foot of a user obviates the need for the user to use his or her hand to contact the medical waste container system 10 in order to open the door 26. Instead, the user merely depresses the lever 114 with his or her foot to open the container 20.

Another preferred feature of the medical waste container system 10 is a mechanism for preventing a user from depressing the lever 114. It has been discovered that such a mechanism helps to prevent unauthorized users from opening the medical waste container by mere operation of the lever 114. Also, it has been discovered that such a mechanism helps to prevent authorized users from operating the lever 114 inadvertently. For example, when the waste container 20 is filled and no additional waste should be introduced into the receptacle 22, a mechanism for preventing a user from depressing the lever 114 helps prevent the inadvertent introduction of additional waste.

In the exemplary embodiment illustrated in FIG. 4, a bracket 116 is mounted to the body 105 of the carrier 100 at its ends for rotation with respect to the body 105 of the carrier 100. More specifically, the bracket 116 can be rotated from a retracted position (shown in FIG. 1) to the extended position shown in FIG. 4. It will be appreciated that, when the bracket 116 is in the locking position shown in FIG. 4, it is difficult or impossible for an unauthorized user to move the lever 114 in a direction indicated by the arrow D3. Inadvertent operation of the lever 114 by authorized users is also discouraged by the bracket 116 when it is in the position shown in FIG. 4.

In order to release the locking function of the bracket 116, the bracket 116 can be rotated in the direction indicated by the arrow D4 and returned to the position shown in FIG. 1. The bracket 116 can be operated by the foot of a user when it is located near the bottom of the carrier 100. Foot operation of the bracket 116 is preferred in order to reduce or eliminate hand contact between the user and the system 10. Alternatively, if the lever 114 and bracket 116 are located for hand operation, the user can position the bracket to block the lever by hand.

Referring now to FIGS. 5A-5F, one preferred embodiment of the body component 105 of the carrier 100 is illustrated. It should be noted that the body 105 could be formed in a wide variety of shapes, configurations, materials, sizes, and proportions. The shape and configuration of the body 105 are not dictated by its function. Instead, the configuration of the body 105 provides the carrier 100 with an ornamental appearance that is appealing to the eye.

The body 105 is preferably formed from plastic such as polyethylene (PE) for example, most preferably linear low density polyethylene (LLDPE), but a metallic body is also contemplated. Preferably, when the body 105 is formed from plastic, the body 105 is preferable formed by a molding process. Most preferably, the body 105 is formed by a rotational molding process.

Figure 5A:
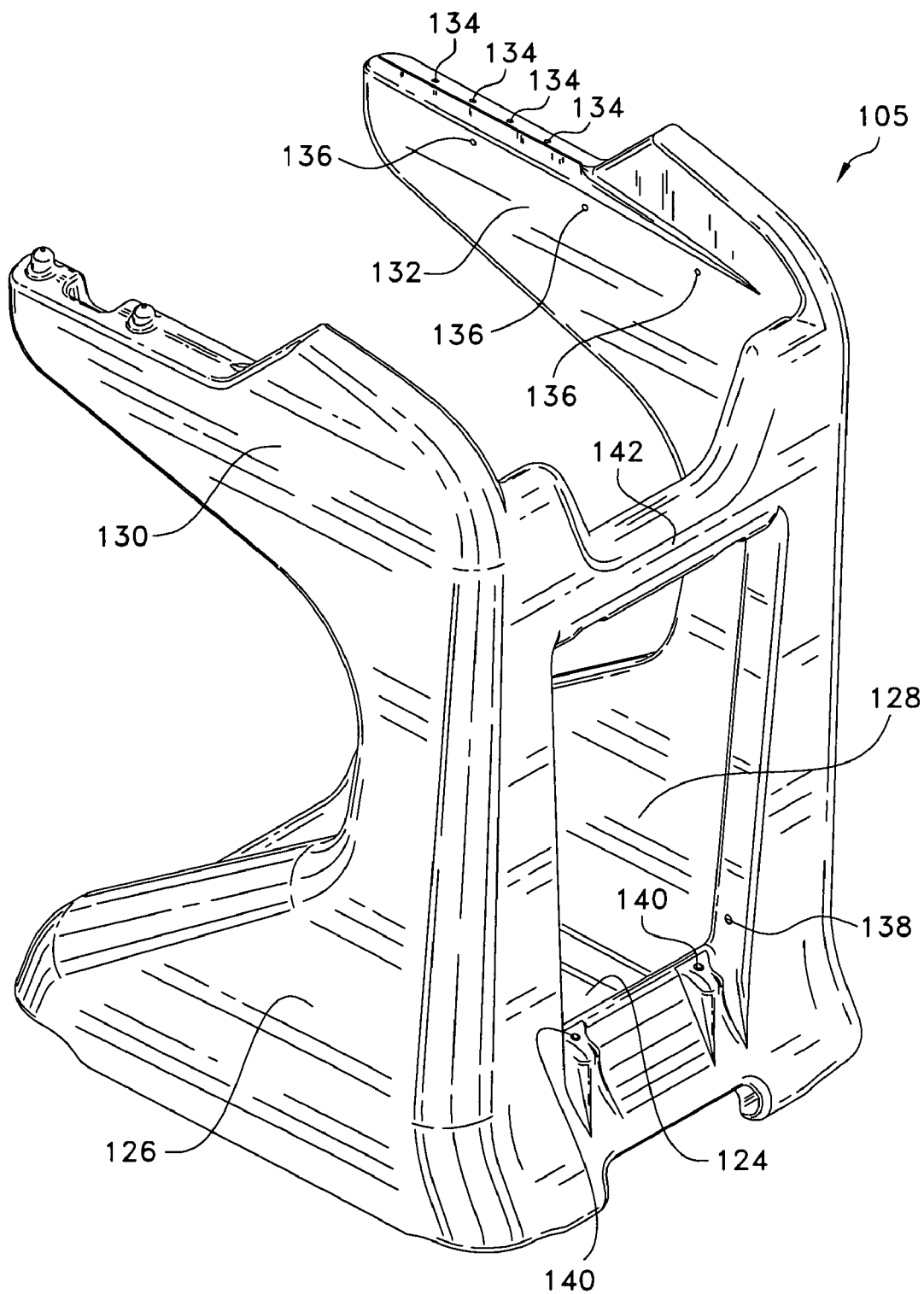
FIG. 5A is a perspective view of an embodiment of a body component of the container system illustrated in FIG. 1.

Referring specifically to the perspective view shown in FIG. 5A, the body 105 of the carrier 100 includes a base portion 124 to which the wheels 112 (shown in FIG. 4) can be mounted. The body 105 also includes a pair of lower side portions 126 and 128, a pair of upper side portions 130 and 132, and an upper front portion 142 that extends between the upper side portions 130 and 132.

The upper side portion 132 of the body 105 is provided with a series of hinge mounting holes 134 (four (4) shown), which facilitate the mounting of the hinge connecting the hood 104 to the body 105. The upper side portion 132 of the body 105 is also provided with a series of guide rail mounting holes 136 (three (3) shown) to facilitate the mounting of the guide rails 102 to the body 105. Only one set of guide rail mounting holes 136 is shown in FIG. 5A, and it will be understood that guide rail mounting holes 136 are also provided on the upper side portion 130 of the body 105.

Toward the base portion 124 of the body 105, a pair of bracket mounting holes 138 (only one shown in FIG. 5A) is provided for the mounting of terminal end portions of the bracket 116 shown in FIG. 4. The mounting holes 138 permit rotation of the bracket 116 with respect to the body 105 from a retracted position (FIG. 1) to an extended position (FIG. 4) and back again. Similarly, a pair of handle guide mounting holes 140 are provided near base portion 124 for mounting the lower portions of the handle guides 118. The mounting holes 144 for the upper portions of the handle guides 118 are shown in FIG. 5C and will be described later.

Figure 5B:
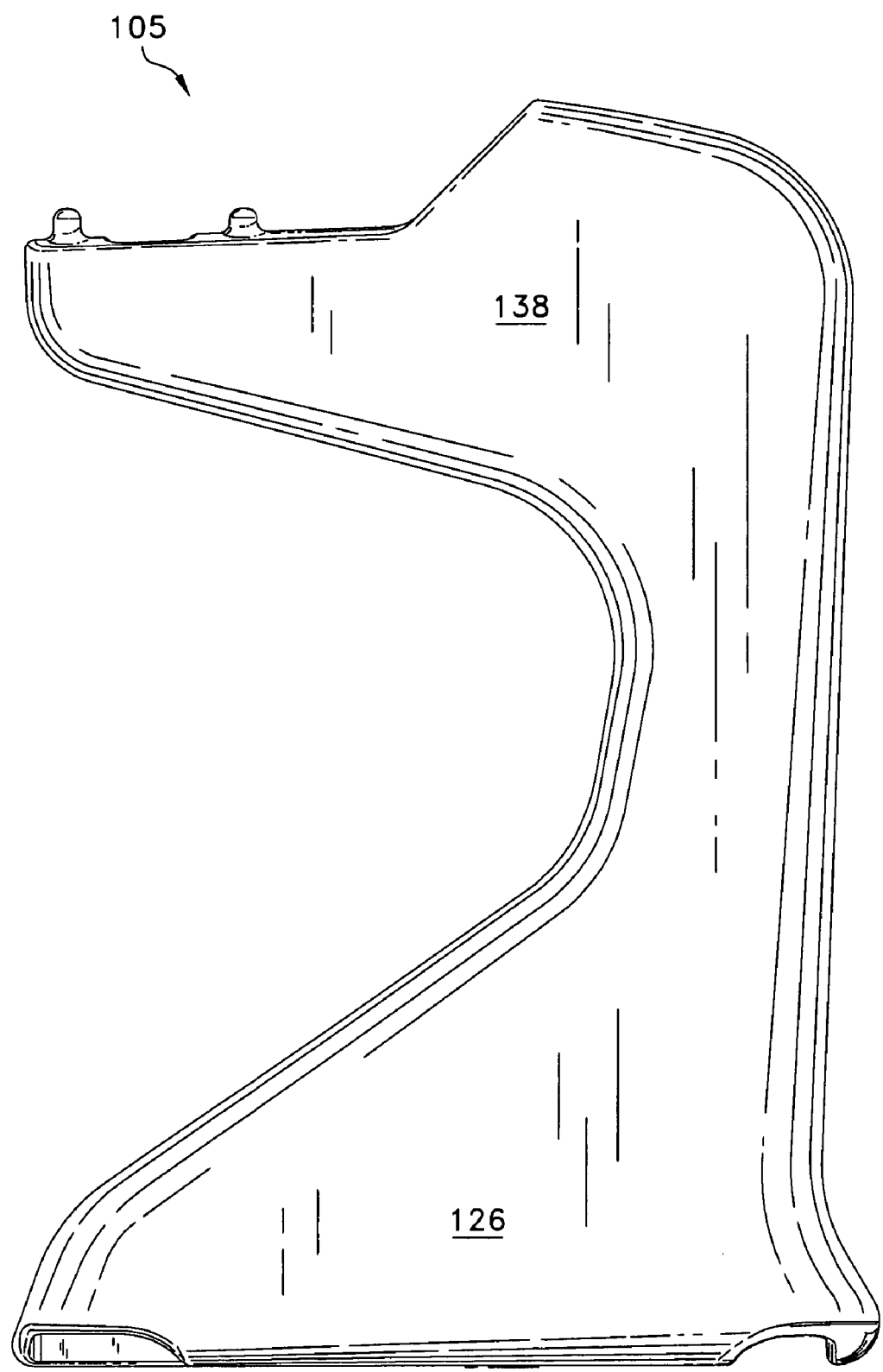
FIG. 5B is a left side view of the body component illustrated in FIG. 5A.

Referring now to FIG. 5B, a left-hand side view of the ornamental body 105 is illustrated. The ornamental body 105 extends from the lower side portion 126 to the upper side portion 130 in a series of contours.

Figure 5C:
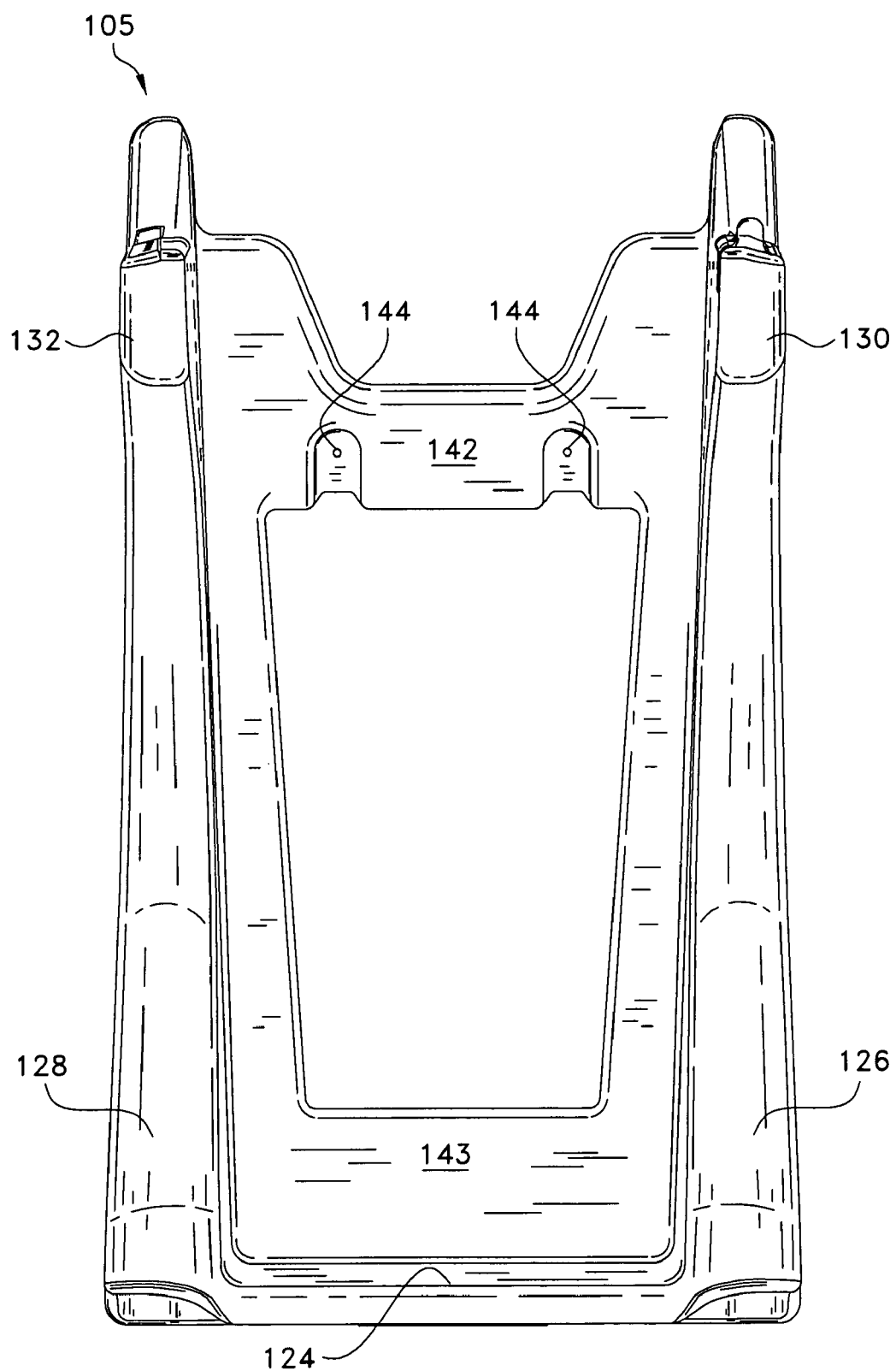
FIG. 5C is a rear view of the body component illustrated in FIG. 5A.

Referring to the rear view of the body 105 illustrated in FIG. 5C, the body 105 includes an ornamental upper front portion 142 that extends between the upper side portions 130 and 132. A pair of handle guide mounting holes 144 is provided on the upper front portion 142 in order to mount the upper portions of the handle guides 118 shown in FIG. 1. A lower front portion 143 of the body 105 extends between the lower side portions 126 and 128.

Figure 5D:
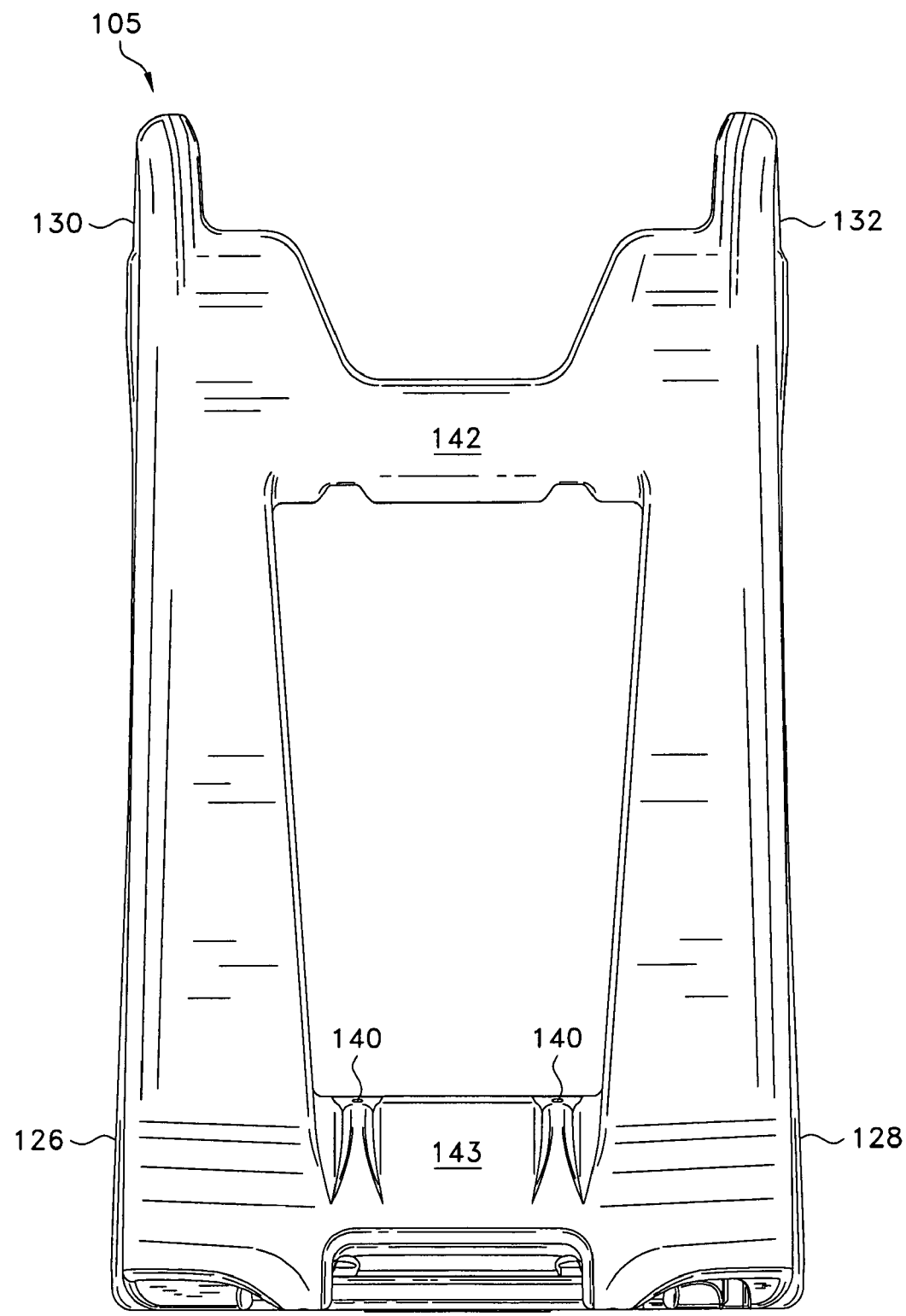
FIG. 5D is a front view of the body component illustrated in FIG. 5A.

FIG. 5D, which provides a front view of the body 105, illustrates additional ornamental features of the upper front portion 142 (extending between the upper side portions 130 and 132 of the body 105) and the lower front portion 143 (extending between lower side portions 126 and 128). Also, FIG. 5D illustrates another view of the handle guide mounting holes 140, which accommodate lower portions of the handle guides 118.

Figure 5E:
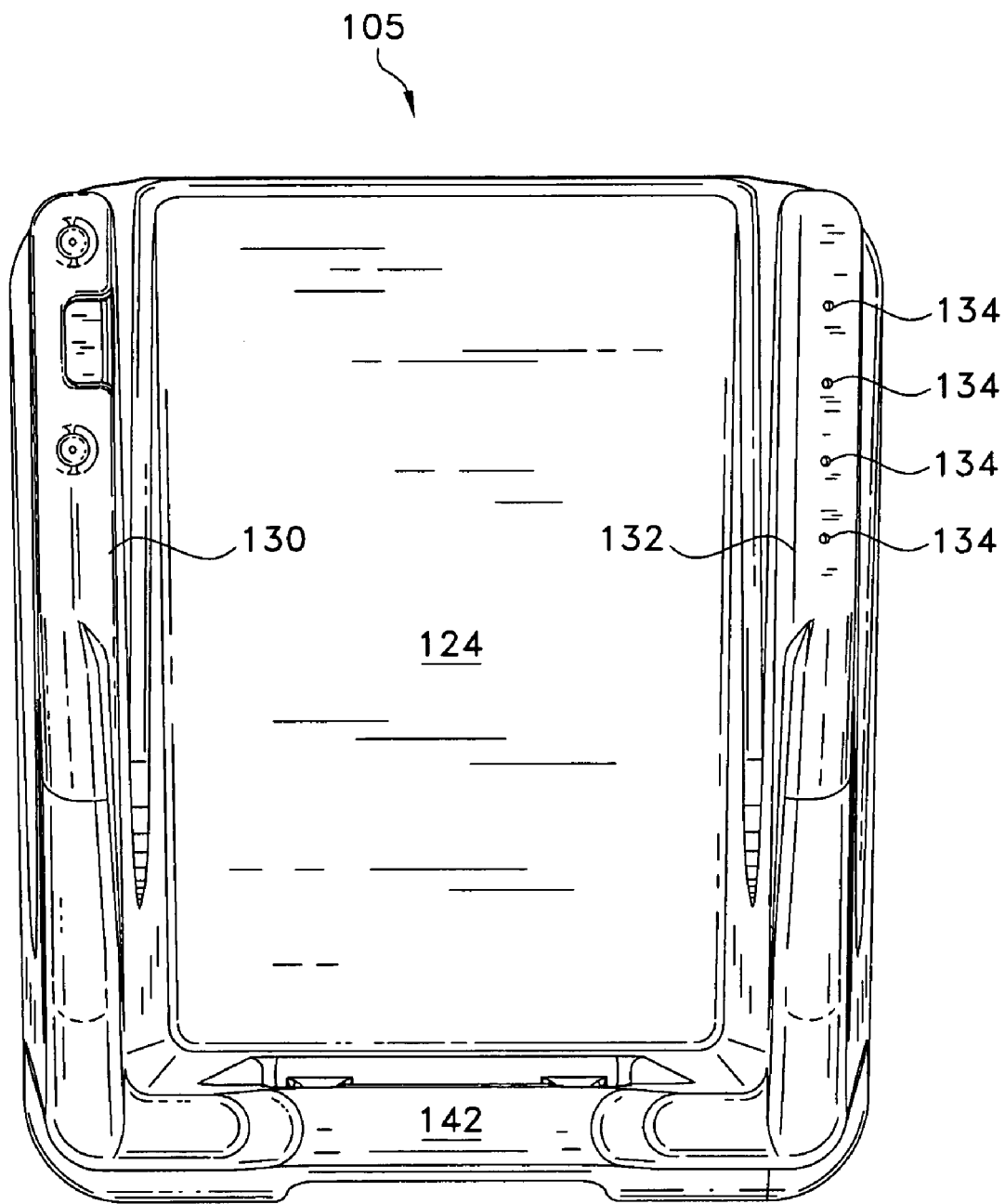
FIG. 5E is a top view of the body component illustrated in FIG. 5A.
Figure 5F:
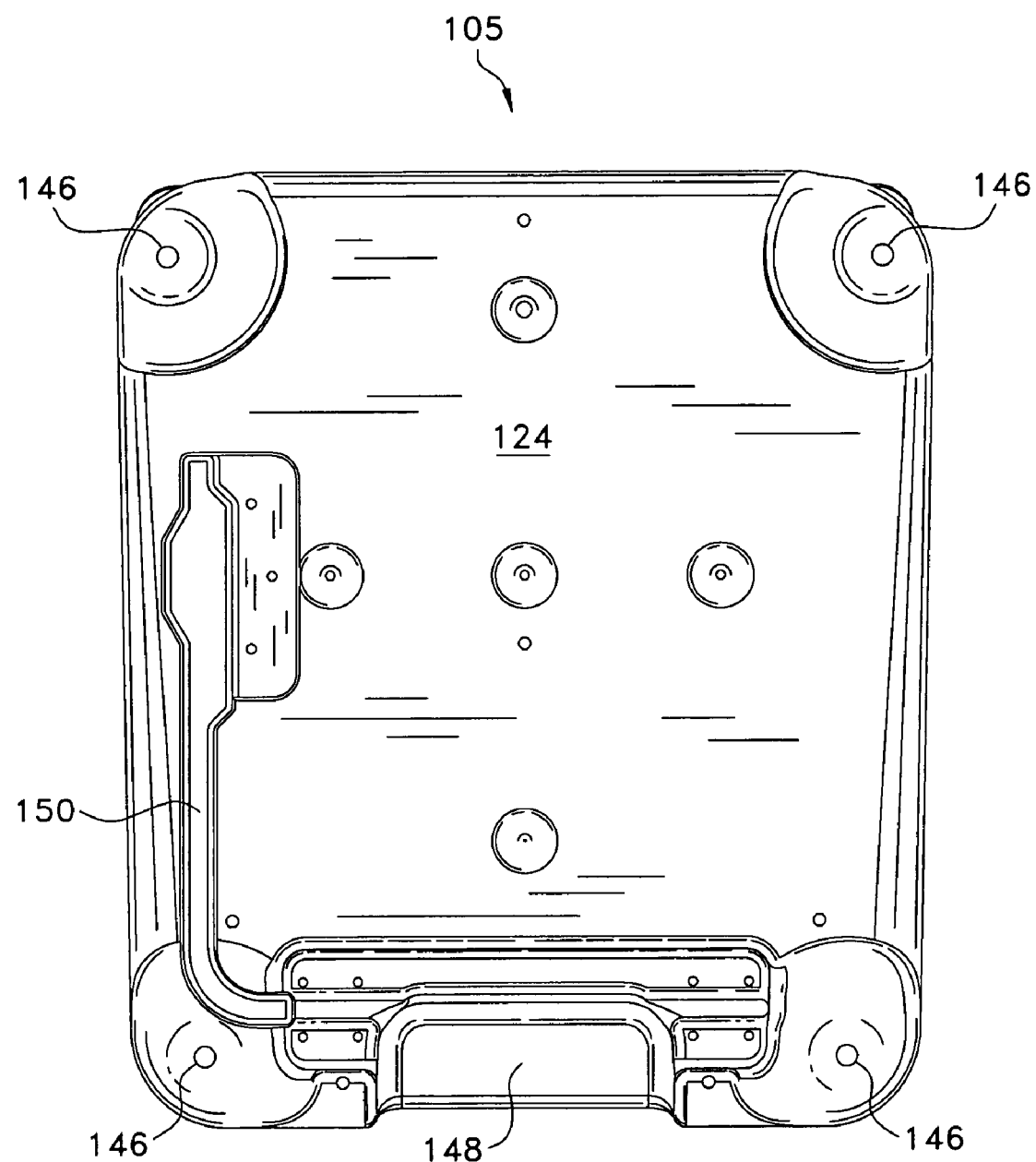
FIG. 5F is a bottom view of the body component illustrated in FIG. 5A.

Top and bottom views of the body 105 are illustrated in FIGS. 5E and 5F, respectively. FIG. 5E reveals additional ornamental features of the upper side portions 130 and 132 and the upper front portion 142 of the body 105. FIG. 5E also illustrates the hinge mounting holes 134 provided in upper side portion 132 of the body 105.

The bottom of body 105 is illustrated in FIG. 5F, which bottom includes four (4) wheel mounting holes 146 to facilitate the mounting of four (4) wheels 112 to the body 105 of the carrier 100. A recess 148 is provided in the bottom surface of the base portion 124 of the body 105 in order to accommodate the lever or foot pedal 114. The lever 114, when mounted to the base portion 124 of the body 105 as illustrated in FIG. 4, can reciprocate by rotation about an axis defined by a portion of the foot pedal that runs perpendicular to the direction in which the lever 114 is depressed. That portion of the lever 114 extends through a recess 149, and a pair blocks (not shown), each attached to the body 105 by a set of four (4) fasteners, captures the lever 114 so that its movement is limited to rotational movement about the axis of the recess 149.

Another portion of the lever 114 (not shown) extends perpendicularly with respect to axis about which the lever 114 rotates. More specifically, that portion of the lever 114 is oriented to extend through a channel 150 in the base portion 124. That portion of the lever 114 moves upwardly when the lever 114 is depressed by the foot of a user. By doing so, as will be described in further detail later, the lever 114 retracts a cable (not shown), thereby actuating the carrier 100 to open the door 26 of the medical waste container 20.

Figure 6C:
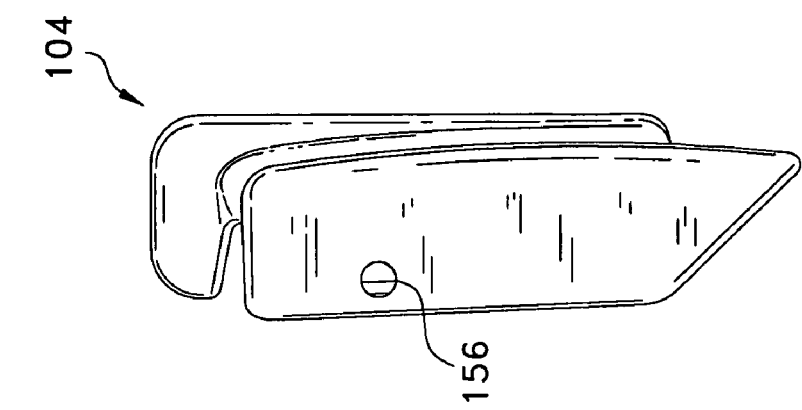
FIG. 6C is left side view of the hood component illustrated in FIG. 6A.
Figure 6A:
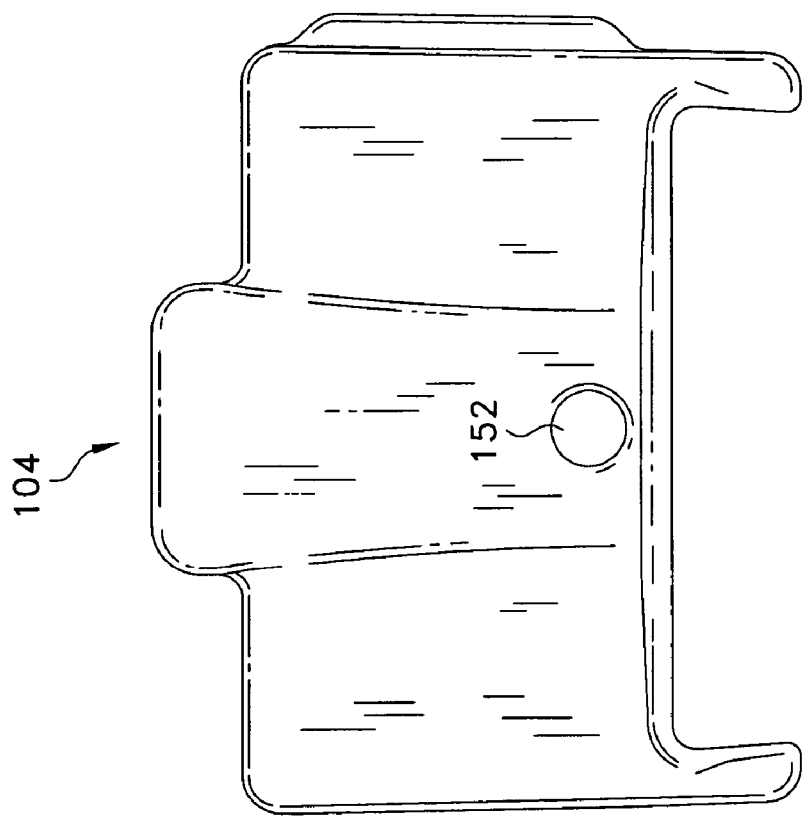
FIG. 6A is a top view of an embodiment of a hood component of the container system illustrated in FIG. 1.
Figure 6B:
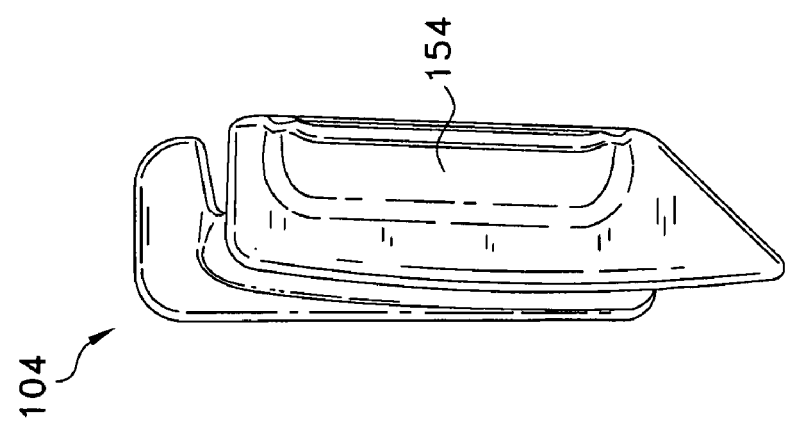
FIG. 6B is a right side view of the hood component illustrated in FIG. 6A.

Referring now to FIGS. 6A-6C, preferred ornamental features of the hood component 104 of the carrier 100 will now be described. Referring first to the plan view shown in FIG. 6A, the hood 104 includes an aperture 152 through which a button (shown in FIG. 7) extends. As is illustrated in the right-side view shown in FIG. 6B, the hood 104 is preferably provided with an integral hinge stop 154. More specifically, hinge stop 154, which can be formed integrally with the hood 104, provides a limit to the hood's rotation when the hood 104 is fully opened. It will be understood that, when the hood 104 is opened to the position shown in FIG. 3, a surface of the hinge stop 154 will contact an upper, outer surface of the upper side portion 132, thereby preventing over-extension of the hinge. Finally, referring to the left-side view illustrated in FIG. 6C, the hood 104 is provided with an aperture 156 for receiving the lock 110.

The hood 104 also includes a container retainer portion 111, which prevents removal of the container 20 from the carrier 100 when the hood 104 is in the closed position. The retainer portion 111 is preferably formed integrally with the hood 104, but can take a wide variety of shapes, sizes and configurations.

Like the body 105, the hood 104 is preferably formed from plastic in a rotational molding process. It will be appreciated, however, that the configuration of the hood 104 can take a wide variety of forms, and that the contours selected for the hood 104 contributes to the overall ornamental appearance of the medical waste disposal system 10.

Figure 7:
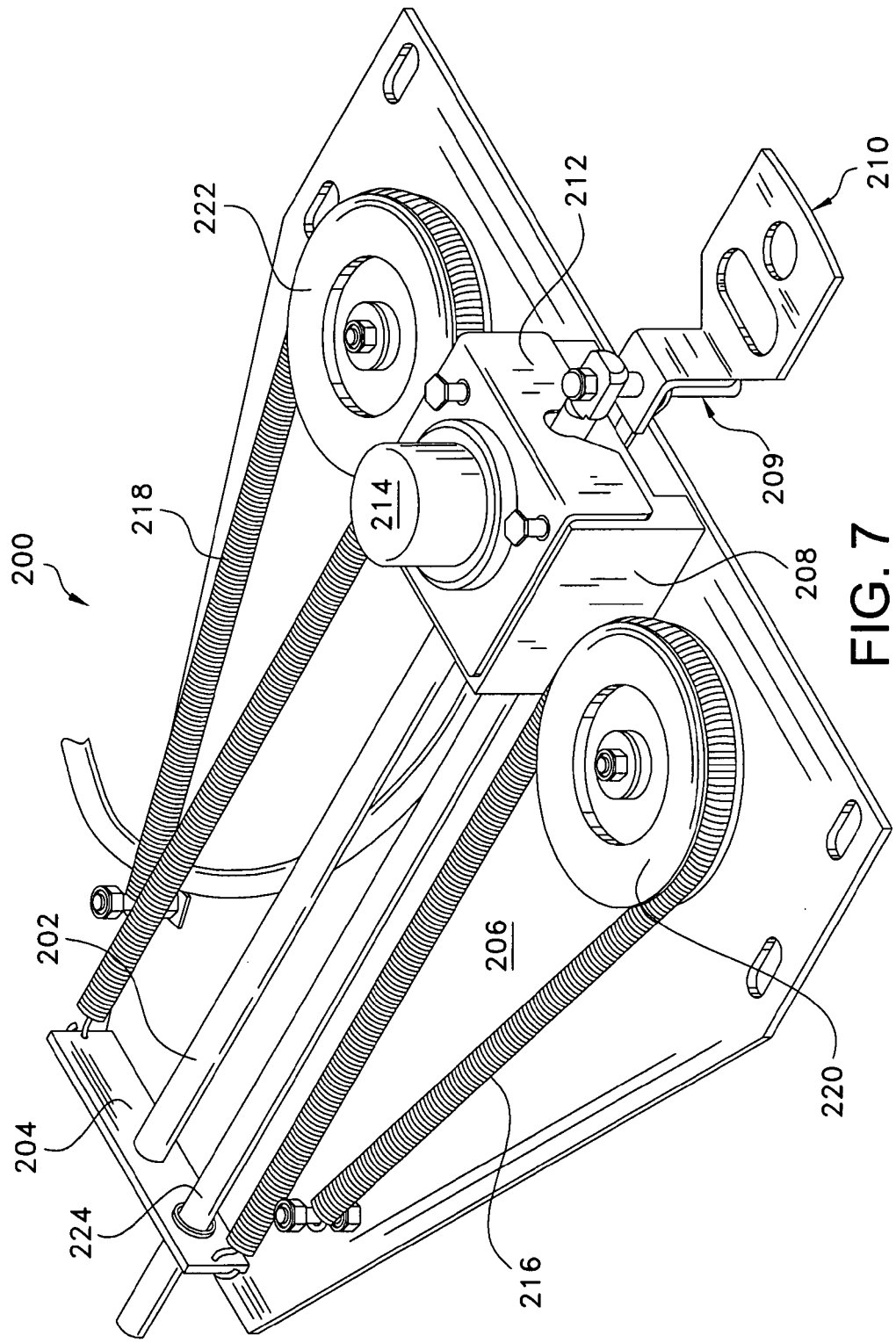
FIG. 7 is a perspective view of an embodiment of an extension or arm control assembly adapted for use in the container system illustrated in FIG. 1.

FIG. 7 illustrates details of one embodiment of a mechanism that can be employed to open and close the door 26 of the medical waste container 20 by operation of the lever 114. As is illustrated in FIGS. 3 and 7, an extension or arm control assembly 200 (FIG. 7) of the door retractor assembly 108 (FIG. 3) is mounted to the hood 104 of the carrier 100.

The arm control assembly 200 includes an extension or arm 202 that is mounted at its end to a bracket 204. The arm 202 extends parallel to a mounting plate 206 and extends through a mounting block 208 that is attached to the plate 206. A pin 209 is attached at the end of the arm 202 opposite from the bracket 204, and an optional bracket 210 is attached to the pin 209 for engagement with the door 26 of the lid 24 of the medical waste container 20. The pin 209 is provided to engage the door of the container. More specifically, the pin 209 extends into the upwardly extending recess 28 formed in the door 26 of the lid 24.

The bracket 210 is one embodiment of an extension of the arm 202 that can be used to adapt the arm control assembly 200 of the system 10 for use with a variety of containers. For example, containers having a configuration different from that of container 20 can be installed in the carrier 100, and an extension such as bracket 210 can be used to couple the arm 202 to the lid of the container. Accordingly, it will be understood that the door 26 of the lid 24 is reciprocated between opened and closed positions as the arm 202, pin 209, and optional bracket 210 of the arm control assembly 200 reciprocate with respect to the hood 104 of the carrier 100.

It is preferred for the carrier 100 to include a mechanism that enables a user of the system 10 to lock the door 26 of the medical waste container 20 in the opened position so that sharps can be introduced into the receptacle 22 of the medical waste container 20 without repeated openings of the container 20 or continuous depression of the foot pedal or lever 114. To accomplish this preferred function, the arm control assembly 200 is provided with a locking member 212 which is mounted for movement with respect to the block 208 so that the locking member 212 can be moved towards the plate 206 of the arm control assembly 200. Preferably, one or more springs are used in the arm control assembly 200, interposed between surfaces of the block 208 and the locking member 212, in order to bias the locking member 212 vertically away from the plate 206.

A button 214 is engaged to a surface of the locking member 212, preferably by means of an aperture (not shown) provided in the locking member 212, and is configured to extend upwardly through the aperture 152 provided in the hood 104 (FIG. 6A). A user of the system therefore has access to the button 214 so that the button 214 and locking member 212 can be depressed, thereby locking the arm 202 of the arm control assembly 200 in a retracted position in order to maintain the door 26 of the medical waste container 20 in the opened position.

Preferred features and the operation of the locking mechanism of the arm control assembly 200 will now be described in greater detail with general reference to FIGS. 7-9. As is illustrated in FIG. 8, the arm 202 of the arm control assembly 200 includes a mounting portion 226 to which the pin 209 is connected (e.g., by threaded fasteners). The arm 202 also includes a recess or a reduced diameter portion 228 and is spaced from the mounting portion 226.

Referring now to FIG. 9, which illustrates preferred features of the locking member 212 of the arm control assembly 200, the locking member 212 includes a pair of mounting holes 230 on a mounting portion 232 in order to facilitate the connection between the mounting member 212 and the block 208 of the arm control assembly 200.

The locking member 212 also includes a locking recess 234 on a locking portion 236. Locking recess of 234 of locking member 212 facilitates releasable engagement between the locking member 212 and the arm 202 of the arm control assembly 200 when the button 214 and locking member 212 are depressed by a user of the system 10 toward the plate 206 of the arm control assembly 200. More specifically, referring again to FIG. 7, the arm 202 of the arm control assembly 200 is preferably biased into the extended position (not shown in FIG. 7) wherein the arm 202 extends outwardly from the hood 104 as is shown in FIG. 3. More specifically, arm control assembly 200 includes a pair of coiled tension springs 216 and 218 which are mounted with respected to the plate 206 by means of two guides 220 and 222, respectively, which are mounted directly to the plate 206. A guide rod 224 may also be provided in the arm control assembly 200 in order to guide the end of the arm 202 that is connected to the bracket 204 as the arm 202 extends from the retracted position shown in FIG. 7 to the extended position shown in FIG. 3 and to keep the pin 209 in a vertical orientation.

By virtue of the springs 216 and 218 of the arm control assembly 200, the arm 202 is biased toward the extended position shown in FIG. 3 in that the springs 216 and 218 pull upon the bracket 204, thereby urging an extension of the arm 202 through the block 208 of the arm control assembly 200. When the button 214 and locking member 212 are depressed by a user of the system 10 while the arm 202 is in the retracted position shown in FIG. 7 (i.e., while the lever 114 is depressed and while the door 26 of the container is in the opened position), the locking recess 234 extends into the reduced diameter portion 228 of the arm 202 (FIG. 8). By virtue of the bias of the arm 202 towards the extended position after the lever 114 is released, it will be understood that a facing surface of the reduced diameter portion 228 is urged against a surface of the locking portion 236 of the locking member 212 that is adjacent to the locking recess 234.

Although not shown in FIG. 9, the hidden surface of the locking portion 236 is preferably provided with a counterbore in the radiused portion of the locking recess 234, thereby facilitating greater frictional contact between the facing surface of the reduced diameter portion 228 of the arm 202 and the locking portion 236 of the locking member 212. The button 214 can be released by the user of the system 10, and the fictional engagement between the locking member 212 and the arm 202 will retain the arm 202 in the retracted position shown in FIG. 7.

When a user desires to release the arm 202, thereby allowing the carrier 100 to return the door 26 of the container 20 to the closed position, the user can actuate the lever or foot pedal 114 once again in order to release the engagement between the locking member 212 and the arm 202. More specifically, by actuating the lever 114 to retract the arm 202 farther into the hood 104, the fictional engagement between the locking member 212 and the arm 202 is broken, thereby permitting the button 214 and locking member 212 to return to their original position by action of the springs (not shown) that are interposed between the locking member 212 and the block 208.

Referring now to FIG. 10, a cable assembly 238 of the carrier 100 is illustrated. The cable assembly 238 is provided to couple the lever or foot pedal 114 to the arm 202 and/or pin 209 of the arm control assembly 200. More specifically, depressing the lever 114 downwardly in the direction D3 shown in FIG. 4 retracts the cable assembly 238 against the bias provided by springs 216 and 218 of the arm control assembly 200. In other words, as the lever 114 is actuated, the cable assembly 238 pulls the assembly of the arm 202, pin 209 and optional bracket 210 towards the retracted position shown in FIG. 7.

The cable assembly 238 preferably travels through a plastic conduit assembly in order to protect the cable and to reduce the wear between the cable and the components of the carrier 100. The cable assembly 238 extends through the body 105 of the carrier 100 from the lever 114 and through the hood 104 to the assembly of the arm 202, pin 209 and optional bracket 210.

One preferred embodiment of the cable assembly 238 is illustrated in FIG. 10. The cable assembly 238 includes an eyelet 240 connected to a lubricated metallic cable 242. The lubricated cable 242 extends through a conduit assembly including a pair of threaded conduit fittings 244, a plastic conduit 246, external tooth lockwashers 248, and jam nuts 250. The lubricated cable 242 extends outwardly from the opposite end of the conduit assembly and terminates at another eyelet 252. It will be understood that one end of the cable assembly 238 (e.g., eyelet 240 or 252) is coupled to the lever 114, and the other end of the cable assembly 238 (e.g., eyelet 252 or 240) is coupled to the arm control assembly 200. Accordingly, the cable assembly 238 couples the lever 114 to the arm control assembly 200 so that the depression of the lever 114 by a user of the system 10 brings about the retraction of the arm 202 of the arm control assembly 200 into the hood 104.

The operation of the medical waste container system 10 will now be described with general reference to FIGS. 1-10. A medical waste container 20 is introduced into the interior region defined by the carrier 100 by releasing the lock 110 on the hood 104, rotating the hood 104 by means of the hinge 106 to open the hood 104, sliding the medical waste container 20 into the interior region defined by the carrier 100 until a portion of the medical waste container 20 is supported by the guide rails 102 of the carrier 100, closing the hood 104, and engaging the lock 110, thereby locking the medical waste container 20 within the carrier 100.

In order to remove a filled medical waste container 20 from the carrier 100, the foregoing steps are substantially reversed. Specifically, the lock 110 on the hood 104 is disengaged, the hood 104 is again rotated by means of the hinge 106 into an open position, and the filled medical waste container 20 is then removed in the direction D2 shown in FIG. 3.

In order to open the medical waste container 20 using the system 10 (e.g., in order to deposit waste in the receptacle 22 of the container 20), the lever or foot pedal 114 is depressed by a user in a direction D3, thereby causing the arm 202 to retract into the hood 104 of the carrier 100 and causing the door 26 of the medical waste container 20 to slide into the opened position. Medical waste can then be deposited through the opening in the lid 24 of the medical waste container 20 for receipt in the receptacle 22.

In order to lock the door 26 of the medical waste container 20 in the open position after the depression of the lever 114 in the direction D3, the button 214 of the arm control assembly 200 can be depressed by the user and the lever 114 can be released in order to bring about engagement between the locking member 212 of the arm control assembly 200 and a surface of the reduced diameter portion 228 of the arm 202 of the arm control assembly 200. While the medical waste container 20 is locked in this opened position, a user of the system 10 need not depress the lever 114 (which will remain in the depressed position by virtue of the cable assembly 238 and the engagement between the locking member 212 and the arm 202), and the user can deposit medical waste in the medical waste container 20 through the open door 26.

In order to release the button 214 of the arm control assembly 200, thereby releasing the arm 202 and bringing about closure of the door 26, a user can depress the lever 114 farther. By doing so, the frictional interengagement between the locking member 212 and the arm 202 of the arm control assembly 200 is released so that the arm 202 can be extended from the hood 104, thereby allowing movement of the door 26 to the closed position as the lever 114 is released by the user (by virtue of the bias provided by the springs 216 and 218).

In order to prevent unauthorized or unintended use of the system 10 by operation of the lever 114, the bracket 116 can be rotated downwardly to a position corresponding to the lever 114 as is illustrated in FIG. 4. When in that position, the bracket 116 prevents an individual from depressing the lever 114 in the direction D3. Rotation of the bracket 116 upwardly (into the position shown in FIG. 1) permits operation of the lever 114.

Now referring generally to FIGS. 11A through 16D, another embodiment of a container system will be described. The container system illustrated in FIGS. 11A through 16D is similar to the container system described previously except that it is configured for use with containers having hinged closures. Specifically, waste containers having tops with hinged closures are optionally used for the disposal of contaminated items. Examples of such hinged-closure waste containers are available from Tyco Healthcare Group LP of Mansfield, Mass. (see, e.g., Product Nos. 8997, 8980, 8932, 8933, 8998, 8991, 8982, 8985, 8931, and 8989).

The reciprocal movement of the arm of the container system can be movement in a path along a longitudinal axis of the arm, as described for the previous embodiment, or the reciprocal movement of the arm can be movement about a pivot axis, as will be described with reference to FIGS. 11A through 16D.

Referring generally to FIGS. 11A through 16D, the container system 1010 includes a rotationally-molded carrier 1100 that holds a container 1020. The carrier 1100 has a body portion 1105 and a cover portion, upper portion, or hood 1104. One side of the hood 1104 is hinged to the body portion 1105 of the carrier 1104. When the hood 1104 is opened from a first position to a second position, the container 1020 may be inserted into the carrier 1100 or removed.

A pivoting lid 1026 is used to close the top of the container 1020. Medical waste is placed into the top of the container 1020 when the lid 1026 is rotated to the open position. The hood 1104 of the carrier 1100 remains in the closed position when the lid 1026 is rotated between its open and closed positions.

The lid 1026 is opened via a mechanism that extends from a foot pedal 1114 to a hook 1003. Hook 1003 is coupled to an arm 1002. The arm 1002 and hook 1003 are operated by foot pedal 1114 via a cable-pulley mechanism. When a user presses down on foot pedal 1114, hook 1003 pulls edge 1028 of lid 1026 upward. As edge 1028 is pulled upward, the lid 1026 rotates to provide access to the interior of the container 1020 for disposal of medical waste. To close the lid 1026, the user releases the foot pedal 1114.

The cable mechanism for opening lid 1026 includes a cable 1242 that extends in a sheath 1246 from the foot pedal 1114 up through the hollow wall of carrier 1100, into a hollow space defined between the hood 1104 of the carrier 1100 and a plate 1300 until it reaches a cable-pulley mechanism. Plate 1300 supports most of the pulley mechanism and has a rectangular shaped slot 1314. A pivot block 1306 is coupled to plate 1300 on one side of slot 1314, and a second pivot block 1304 is coupled to plate 1300 on the opposite side of (and spaced away from) slot 1314. Pivot block 1306 has a through-hole 1308, and pivot block 1304 has a similar through-hole, which through-holes receive a rotatable rod 1302. A 90 degree pulley 1316 is mounted between pivot blocks 1304 and 1306 and is supported by, and rotated about, rotatable rod 1302. Pulley 1316 is suspended in slot 1314.

Arm 1002 is coupled to rotatable rod 1302, and cable 1242 is coupled to, and winds around, pulley 1316. When a user steps on foot pedal 1114, cable 1242 is pulled, causing pulley 1316 to rotate. This causes arm 1002 to lift the lid 1026 of the container 1020. Preferably, stop surfaces 1090 and 1092 are provided to limit rotational opening movement of lid 1026. When a user releases foot pedal 1114, cable 1242 moves in an opposite direction, causing pulley 1316 to rotate back. This causes lid 1026 to rotate to its closed position.

A cable block 1310 is positioned directly behind pulley 1316 and has a slot 1312 aligned with a center groove 1322 in pulley 1316. The alignment of slot 1312 with center groove 1322 properly aligns cable 1242 with the center groove 1322 to enable substantially effortless rotation of pulley 1316 as cable 1242 is actuated by foot pedal 1114.

A temporary-open block 1320 is mounted onto plate 1300 adjacent to pivot block 1306 and pulley 1316. Temporary-open block 1320 has a through-opening 1318 to receive a rod 1214 and a spring (not shown). Rod 1214 has a first end that extends from one side of block 1320 to a location outside the carrier 1100. Rod 1214 has a second end that extends from the other side of block 1320 toward pulley 1316. Pulley 1316 has a detent (the upwardly extending portion shown in FIG. 16C) coupled to a side of the pulley 1316.

When a user steps on foot pedal 1114, causing pulley 1316 to be fully rotated in the counterclockwise direction (from the perspective of FIG. 16C), the detent coupled to the side of the pulley 1316 is rotated to a position where it has a surface extending substantially parallel to plate 1300. Rod 1214 can then be pushed in a direction toward pulley 1316, causing an end of rod 1214 to be extended over the detent on the side of the pulley 1316, thereby preventing clockwise movement of the detent and pulley 1316 upon release of the foot pedal 1114 by means of frictional engagement and/or interference between the rod 1214 and the detent. Lid 1026 is therefore maintained in the open position. When the foot pedal 1114 is again depressed, frictional engagement between the rod 1214 and the detent is released, and the spring within block 1320 pulls or biases the end of rod 1214 away from the detent, allowing the detent and pulley 1316 to rotate in the clockwise direction, thereby allowing lid 1026 to close.

Figure 11A:
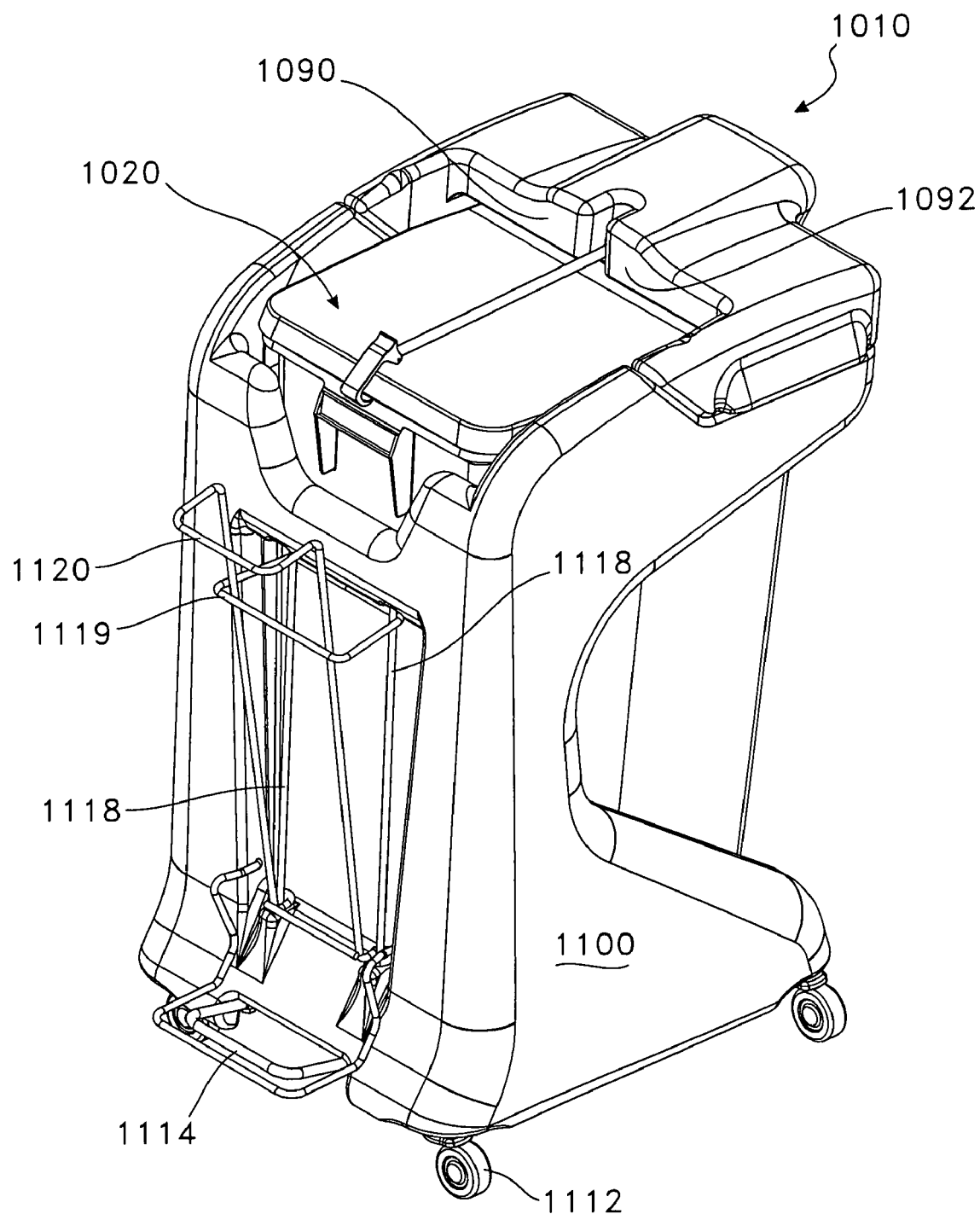
FIG. 11A is a perspective view of another embodiment of a container system according to this invention, with a container door in the closed position.
Figure 11B:
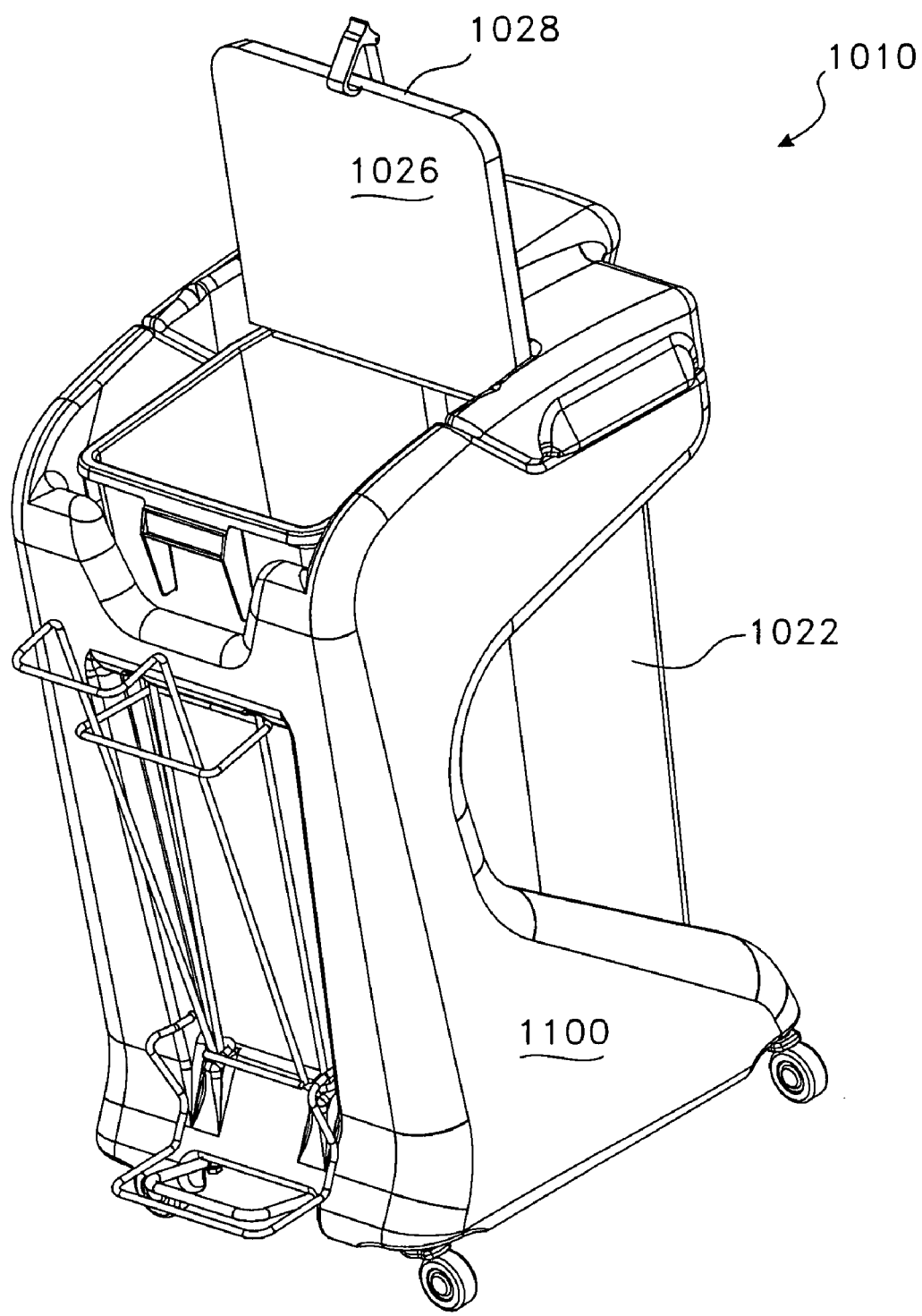
FIG. 11B is a perspective view of the container system shown in FIG. 11A, with the container door in the open position.
Figure 11C:
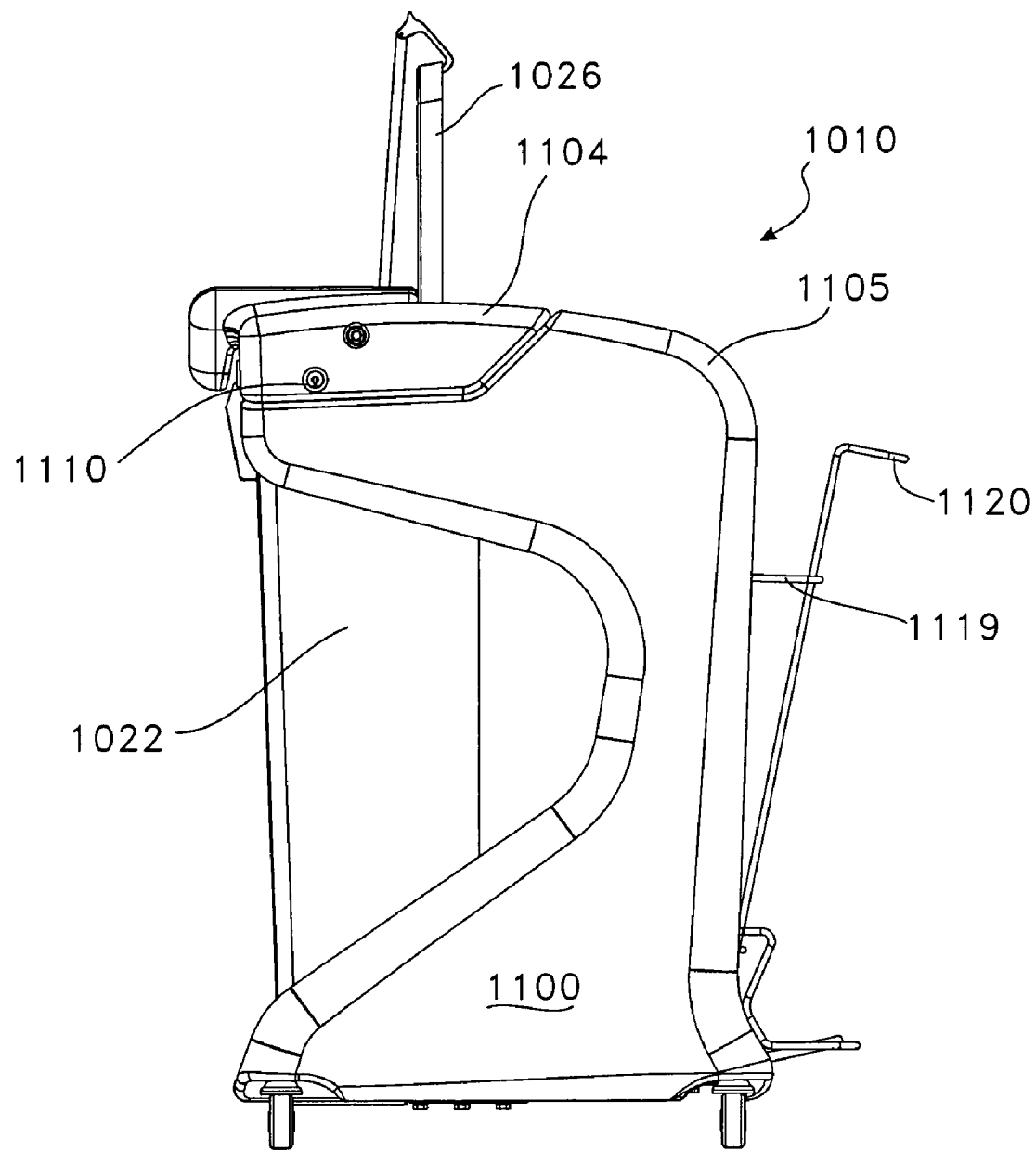
FIG. 11C is a side view of the container system shown in FIG. 11B.

Referring specifically to FIGS. 11A through 11C, like system 10, the medical waste container system 1010 includes a carrier 1100 includes four (4) wheels 1112 mounted at the base of the carrier 1100. An extendable handle 1120 extends upwardly and outwardly from the carrier 1100 along a pair of vertically-extending handle guides 1118. A loop 1119 forms a support against which the upper portion of the handle 1120 rests.

The medical waste container 1020 includes a receptacle 1022 on which a lid is engaged. A door 1026 is mounted for pivotal reciprocation with respect to the remainder of the lid. The body component 1105 of the carrier 1100 includes a pair of opposed guide rails 1102 in order to support the medical waste container 1020 when it is positioned within the interior defined by the carrier 1100. More specifically, the guide rails 1102 provide a pair of supports against which the lip of the receptacle 1022 and/or a skirt of the container's lid can rest.

Figure 12A:
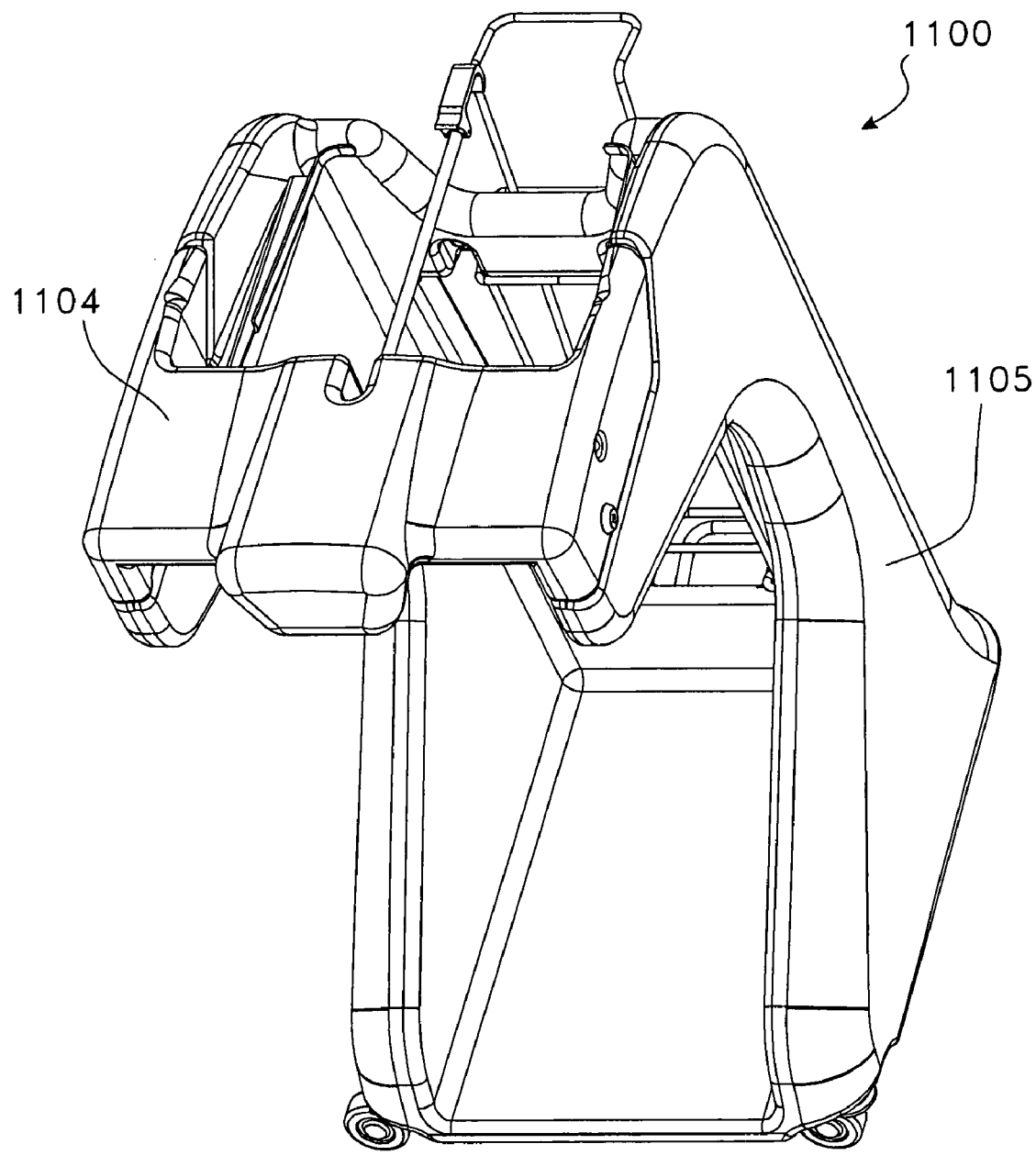
FIG. 12A is a perspective view of the container system shown in FIG. 11A, with the container removed.
Figure 12B:
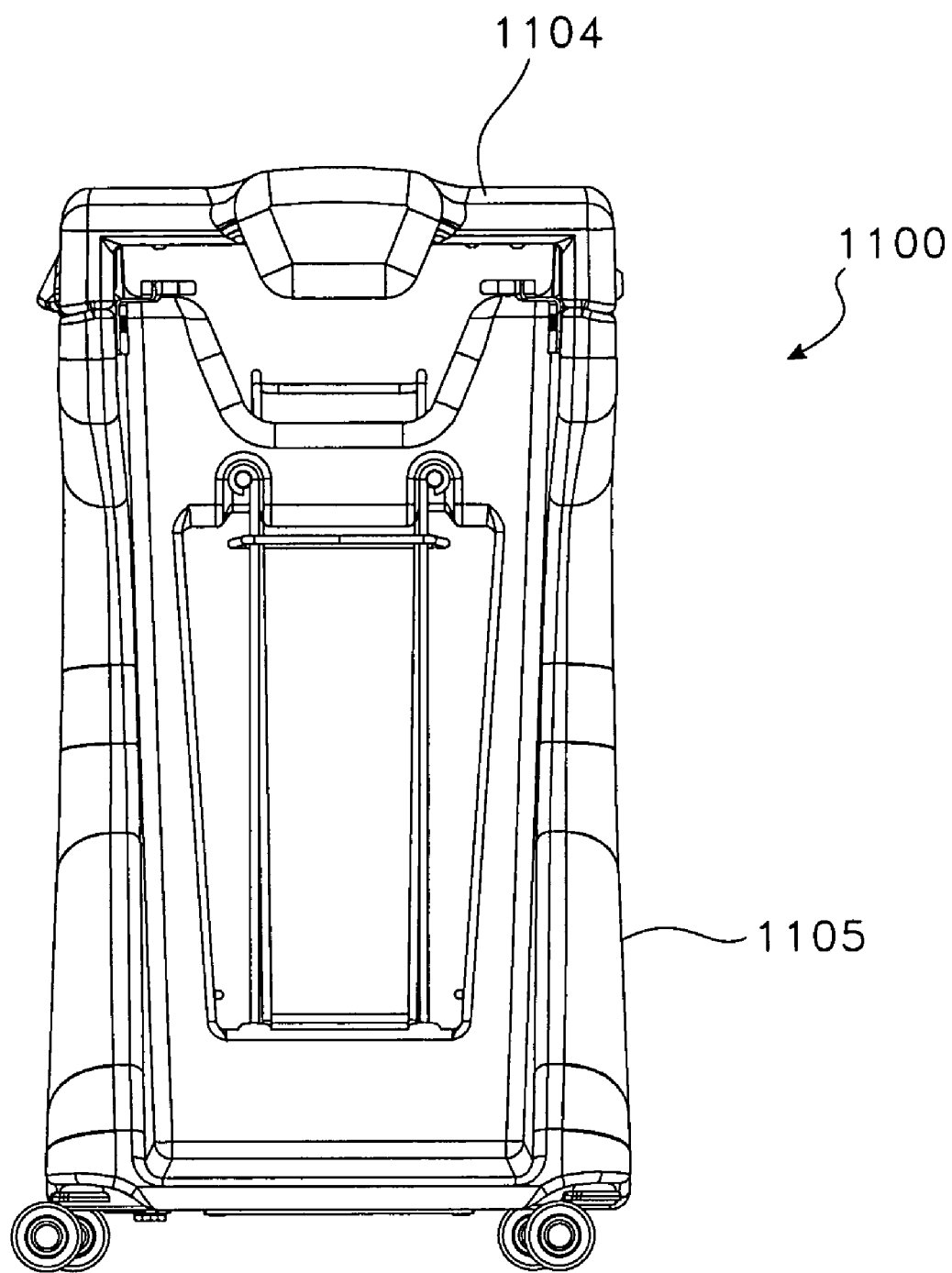
FIG. 12B is a rear view of the container system shown in FIG. 12A, with the container removed.
Figure 12C:
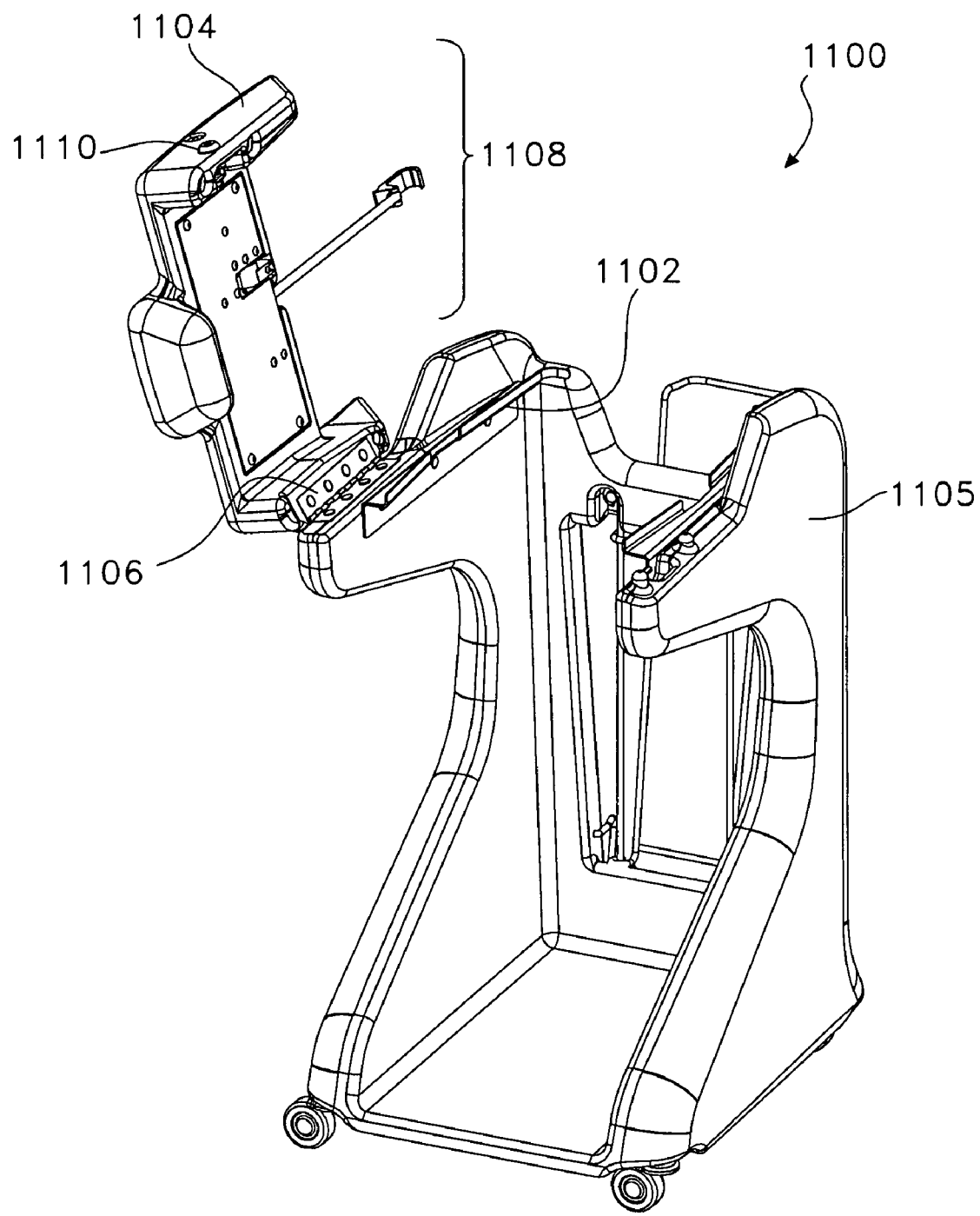
FIG. 12C is a perspective view of the container system shown in FIG. 12A, with the container removed and an upper portion opened.

The carrier 1100 also includes the hood component 1104 that is coupled by means of a hinge 1106 to the body 1105 of the carrier 1100. The hinge 1106 makes it possible to rotate the hood 1104 with respect to the body 1105 so that the hood 1104 can be moved between an opened position (as shown in FIG. 12C) and a closed position (as shown in FIG. 12A). A door retractor or arm control assembly 1108 is used to open and close the door 1026 of the medical waste container 1020, as will be described in further detail later.

When the hood 1104 is closed, removal of the medical waste container 1020 is prevented. Also, a lock 1110 is provided to lock the hood 1104 in a closed position with respect to the body 1105 of the carrier 1100. When the medical waste container 1020 is desired to be removed from the carrier 1100, it can be removed by unlocking the lock 1110 on the hood 1104, rotating the hood 1104 from the closed position to the opened position by virtue of the hinge 1106, and removing the medical waste container 1020. The removal procedure can be reversed in order to introduce the medical waste container 1020, or a replacement container 1020, into the interior defined by the carrier 1100.

The carrier 1100 of the system 1010 includes a lever 1114, such as a foot pedal for example, in order to open and close the door 1026 of the medical waste container 1020. The lever 1114 is depressed downwardly by the foot of a user. A cable 1242 coupled to the lever 1114 runs from the lever, extends through the interior of the hollow body 1105 of the carrier 1100, and is coupled to arm control assembly 1108 for opening and closing the door 1026.

Figure 13:
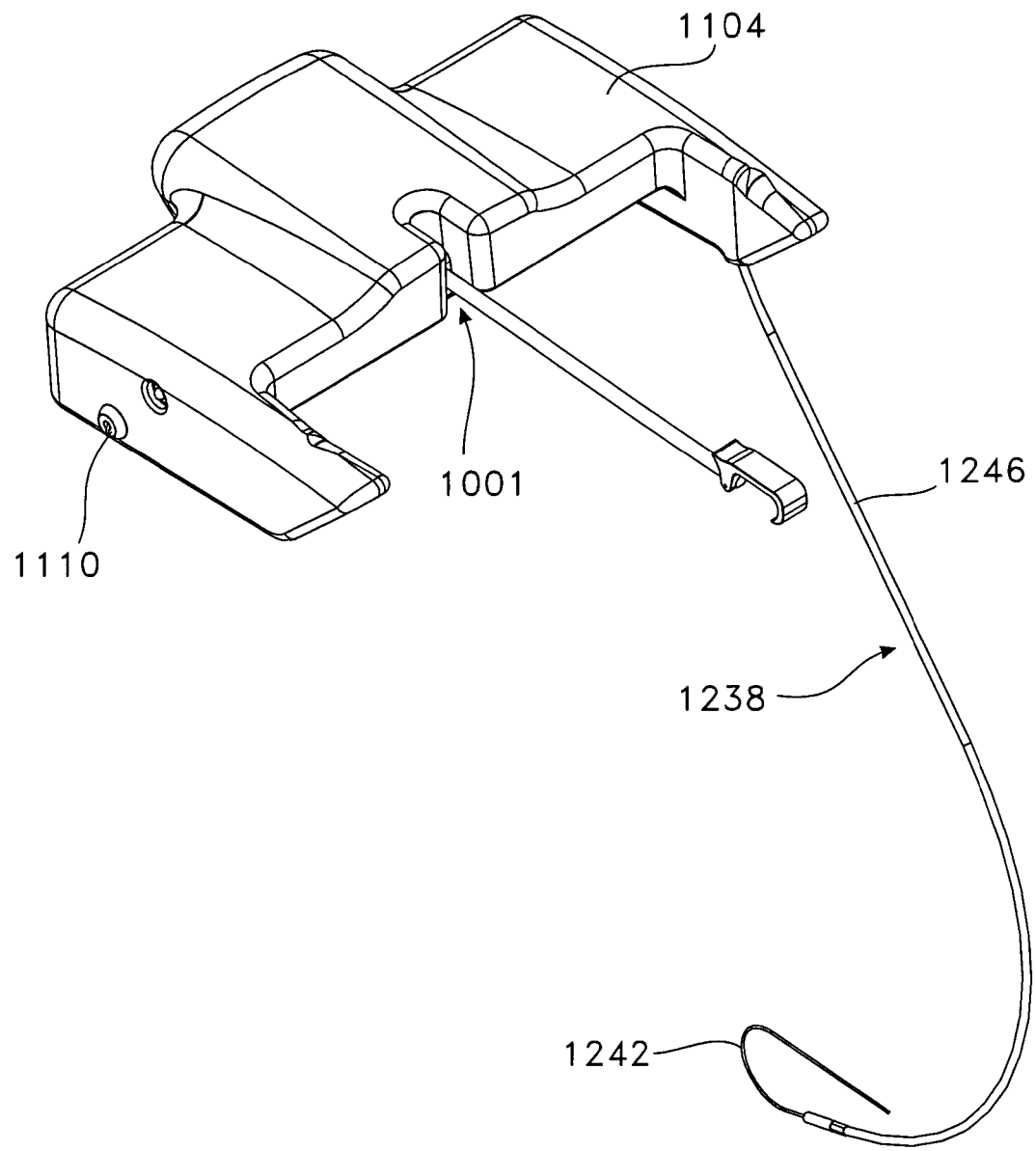
FIG. 13 is a perspective view of an embodiment of an upper portion of the container system shown in FIG. 12A.

Referring to FIG. 13, the hood or upper portion 1104 of the carrier 1100 includes a recessed area 1001 sized, positioned, and shaped to accommodate pivotal movement of the arm assembly. Specifically, hood or upper portion 1104 permits movement of the arm component 1002 from a horizontal position (as shown in FIG. 13) to a vertical position (as shown in FIG. 11C).

As is shown in FIG. 13, the flexible member 1238 includes sheath 1246 through which core 1242 extends. The flexible member 1238 therefore extends through the body portion of the carrier 1100 (not shown in FIG. 13) through a hollow wall portion of the body portion (produced by the rotational-molding process), through the area of the hinge 1106 that connects the body portion 1105 to the hood 1104, and into an interior region of the hood 1104 for coupling to the arm component 1002. By virtue of the hollow wall provided by the rotational molding process, the flexible member 1238 is virtually hidden from exposure to the environment. Because the flexible member 1238 runs through the hollow wall portion of the carrier, it is not exposed to contamination and need not be cleaned. Also, the fact that the flexible member 1238 extends through the hollow wall of the body portion eliminates the need for unsightly mechanisms on an exterior of the body portion.

Figure 14A:
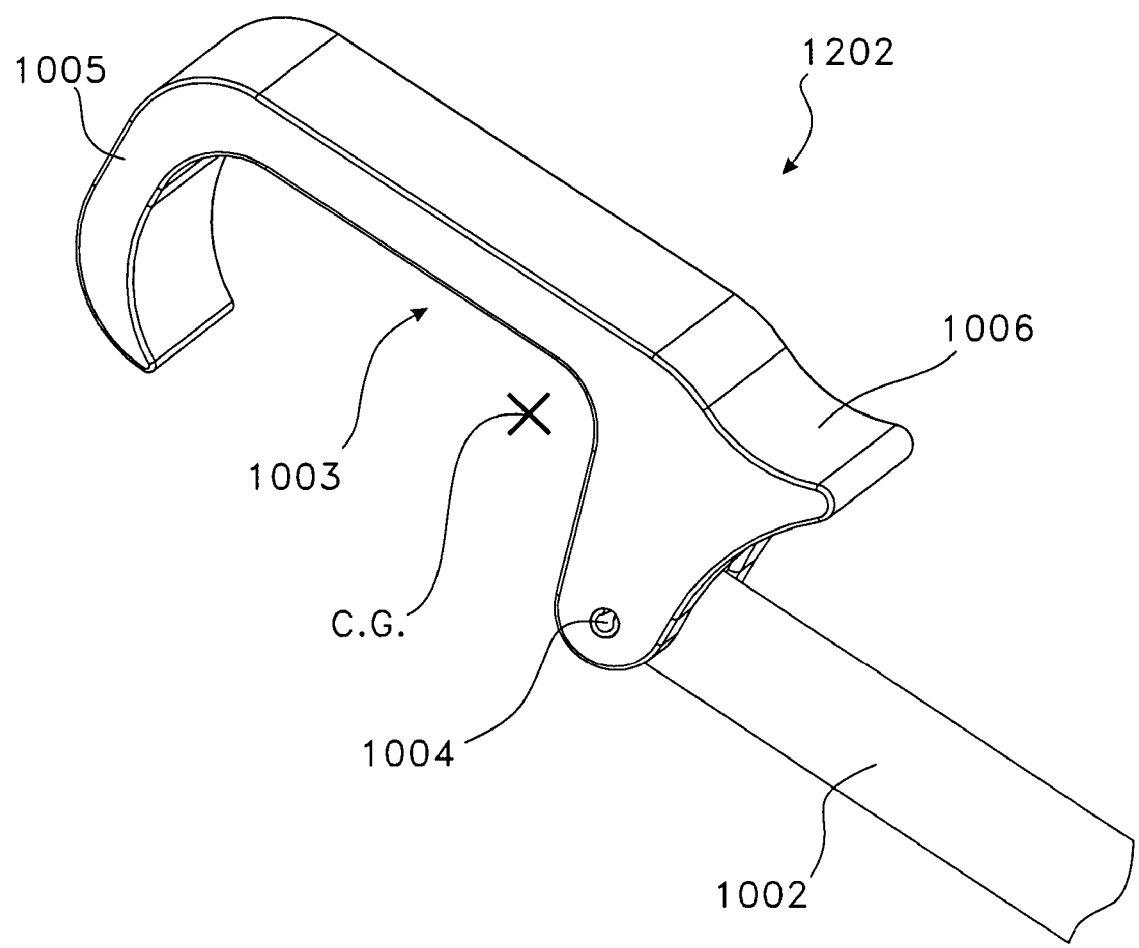
FIG. 14A is a perspective view of an embodiment of a portion of an arm of the container system shown in FIG. 12A.
Figure 14B:
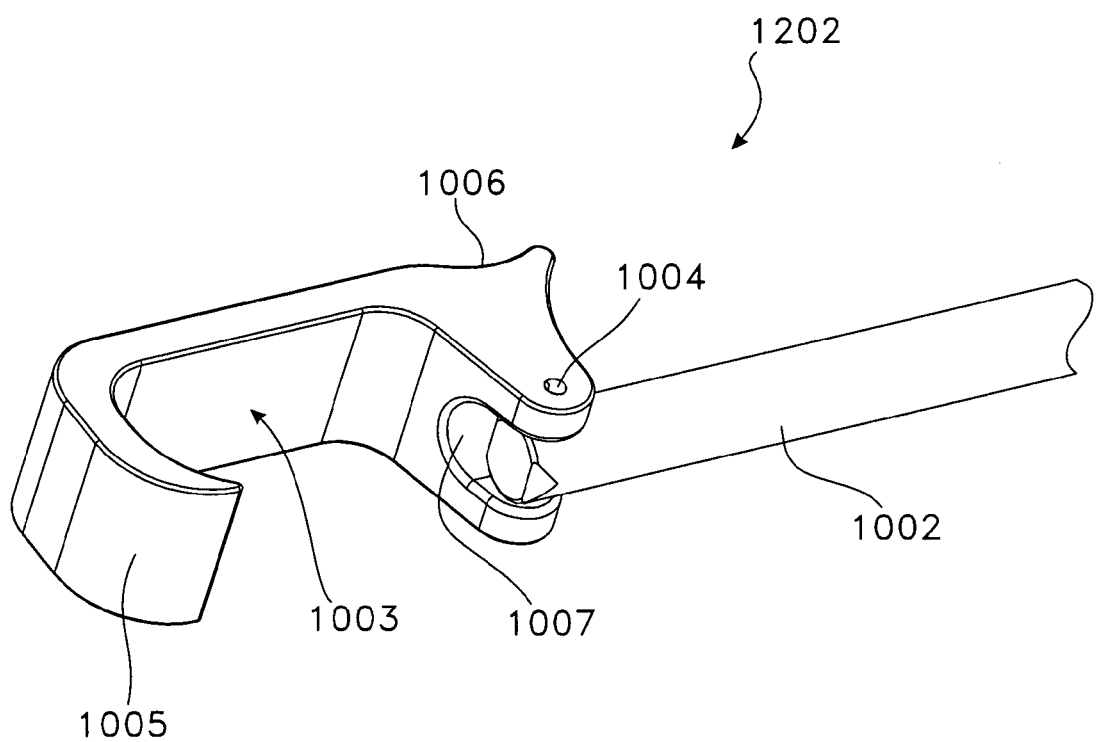
FIG. 14B is another perspective view of the arm portion shown in FIG. 14A.

Referring to FIGS. 14A and 14B, the arm control assembly of the carrier includes an elongated arm member 1002 coupled to a hook portion 1003 by means of a pivotal linkage 1004, which includes a pin in this embodiment. The hook portion 1003 of the arm assembly includes a hooked end 1005. The recess 1006 defines a concave surface by which the hook 1005 can be rotated manually with respect to the elongated member 1002. For example, a user of the carrier can grasp the arm segment 1002 and apply thumb pressure to the recess 1006 in order to rotate the hook 1005 upwardly. By doing so, the position of the hook portion 1003 is moved in order to engage or disengage the hook 1005 with a portion of the door of a container. By depressing the recess 1006, the hook 1005 will disengage an edge 1028 of a container lid. Conversely, by releasing the recess 1006, the hook 1005 preferably is automatically moved by gravity into position for engagement with the edge 1028 of the lid, because the center of gravity C.G. of hook portion 1003 is forward of pivot linkage 1004.

Referring now to FIGS. 11B and 14A, to remove a container 1020 from the carrier 1100, the user depresses the recess 1006 to pivot the hook portion 1003 clockwise to disengage the hook portion 1003 from the edge 1028 of the lid 1026. The user is then able to remove the container 1020 from the carrier 1100. To install a container 1020 into the carrier 1100, the arm segment 1002 is placed in the upright or partially upright position shown in FIG. 11B. The user depresses the recess 1006 of the hook portion 1003 to pivot the hook portion 1003 clockwise to provide clearance for the lid 1026. The user installs the container 1020 into carrier 1100 with the lid 1026 in the open position shown in FIG. 11B. The user then releases recess 1006 of the hook portion 1003. By virtue of the center of gravity C.G. of the hook portion 1003 (the center of gravity C.G. indicated in FIGS. 14A and 15), after the user releases the recess 1006 of the hook portion 1003, the hook portion 1003 naturally pivots counterclockwise to engage with the edge 1028 of the lid 1026.

Figure 15:
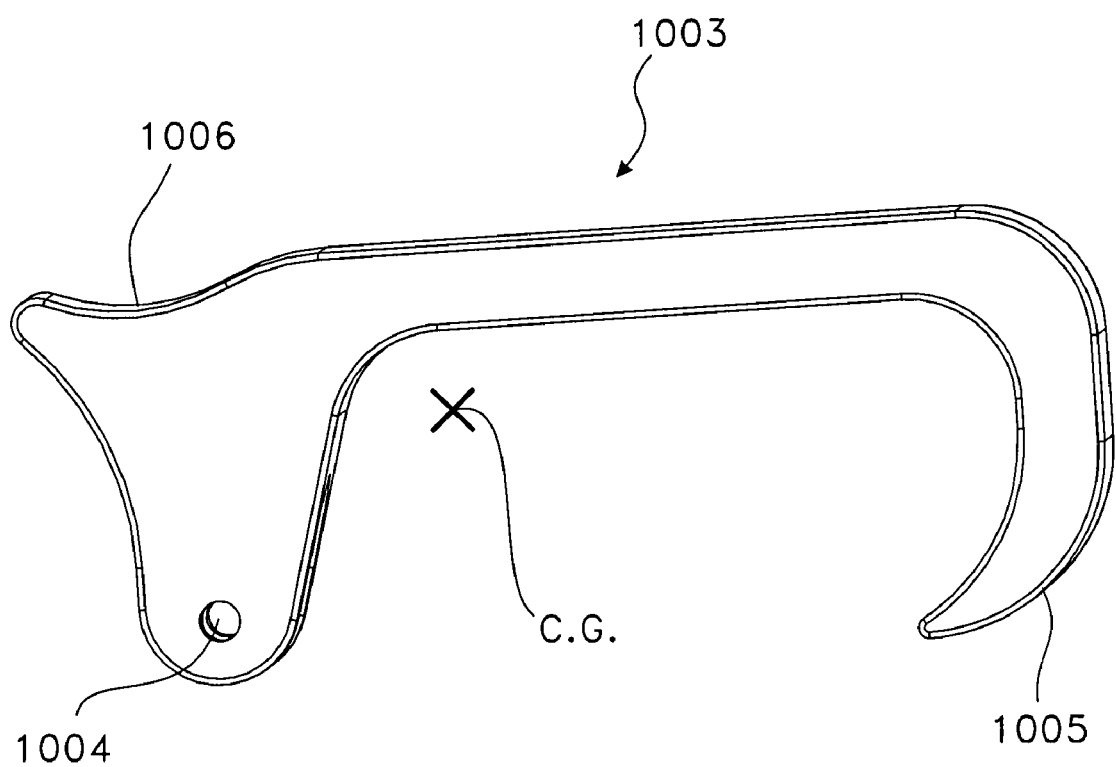
FIG. 15 is a side view of an embodiment of a component of the arm portion shown in FIG. 14A.

As shown in FIG. 14B, the hook portion 1003 includes a recess 1007 that accommodates an end of the elongated portion 1002 of the arm assembly 1202. The recess 1007 permits pivotal movement of the hook portion 1003 with respect to the elongated portion 1002 so that the hook member 1003 can move from a position that is substantially aligned with the axis of the elongated portion 1002 (as shown in FIG. 14B) to a position at which the hook portion 1003 is angled with respect to the elongated portion 1002 (as shown in FIG. 11C). FIG. 15 illustrates additional details of a preferred embodiment of the hook portion 1003.

Referring now to FIGS. 16A through 16D, which illustrate the assembly shown in FIG. 13 but with a shell component of the hood portion 1104 removed to reveal internal details, the manner in which the flexible member 1238 is terminated near the arm member is illustrated. A support member or plate 1300 is mounted within the hood or upper portion 1104 to support the components that control the arm assembly. The elongated arm component 1002 is connected to a pivot member or rotatable rod 1302 that extends along an axis that is substantial parallel to the axis about which the lid of the container pivots. The pivot member 1302 is supported by support members or pivot blocks 1304 and 1306, each of which is coupled to the support member or plate 1300. Component 1306 includes a through-hole 1308 that accommodates one end of the pivot member 1302 while an opposite end of the pivot member 1302 is supported by component 1304.

Another support component or cable block 1310 helps to guide the core 1242 of the flexible member 1238. Specifically, component 1310 includes a channel or slot 1312, which is aligned with a groove 1322 formed in the pulley 1316 that is coupled to the pivot member 1302. Accordingly, the alignment component 1310 aligns the core 1242 so that it travels within the groove 1322 as the arm member 1002 is pivoted.

The pulley 1316 is mounted adjacent an aperture 1314 in the mounting plate 1300. The recess or aperture 1314 therefore permits free rotational movement of the pulley 1316 with respect to the mounting component or plate 1300.

A locking mechanism is provided to lock the arm component 1002 in a position at which the container is opened, thereby maintaining the lid of the container in an open condition even after the foot pedal is released. More specifically, the pulley 1316 includes a surface (shown in FIG. 16C as a vertically-extending detent on the facing surface of the pulley 1316). When the pulley 1316 is rotated by tension of the core 1242, the engagement surface of the pulley 1316 becomes substantially horizontal. In that position, an end of the locking rod 1214 can be pushed through an aperture 1318 formed in a guide component 1320. By doing so, the locking member 1214 engages the detent surface on the pulley 1316 and prevents its rotation back to the position shown in FIG. 16C. The spring (not shown) within the block 1320 urges the locking member 1214 in the opposite direction for release when the food pedal is again depressed.

Figure 16A:
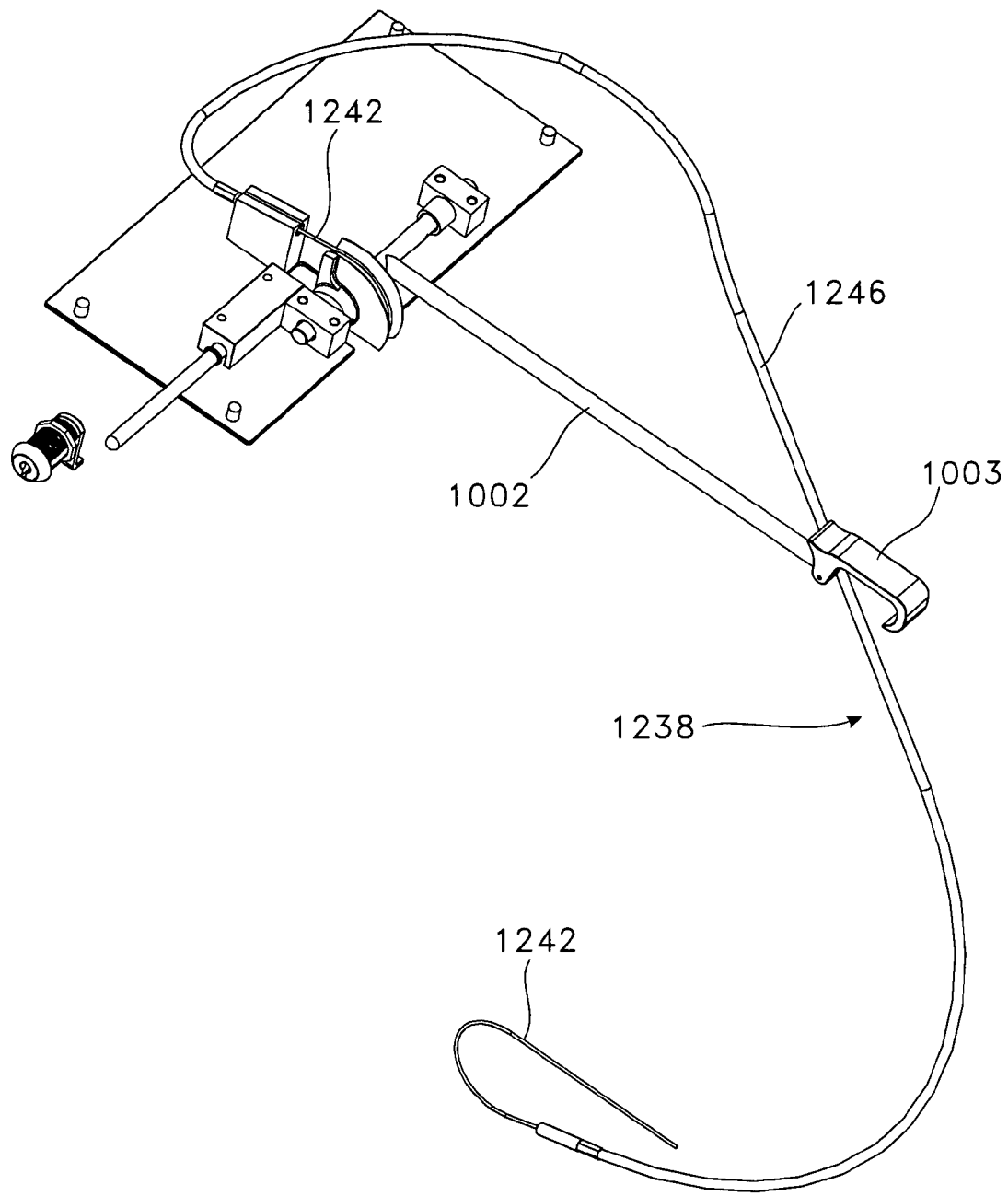
FIG. 16A is a perspective view of the upper portion of the container system shown in FIG. 13, with an outer body portion removed to reveal internal details.
Figure 16B:
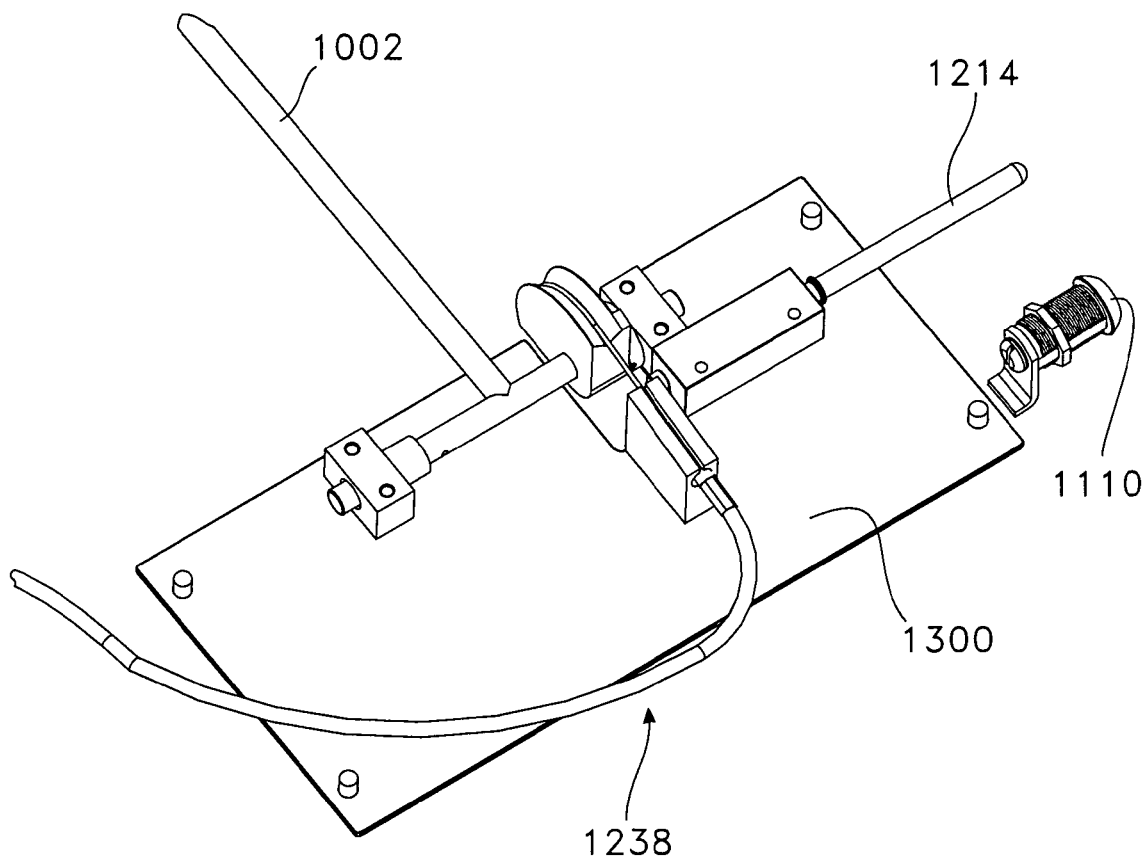
FIG. 16B is another perspective view of the upper portion of the container system shown in FIG. 16A, also with the outer body portion removed to reveal internal details.
Figure 16C:
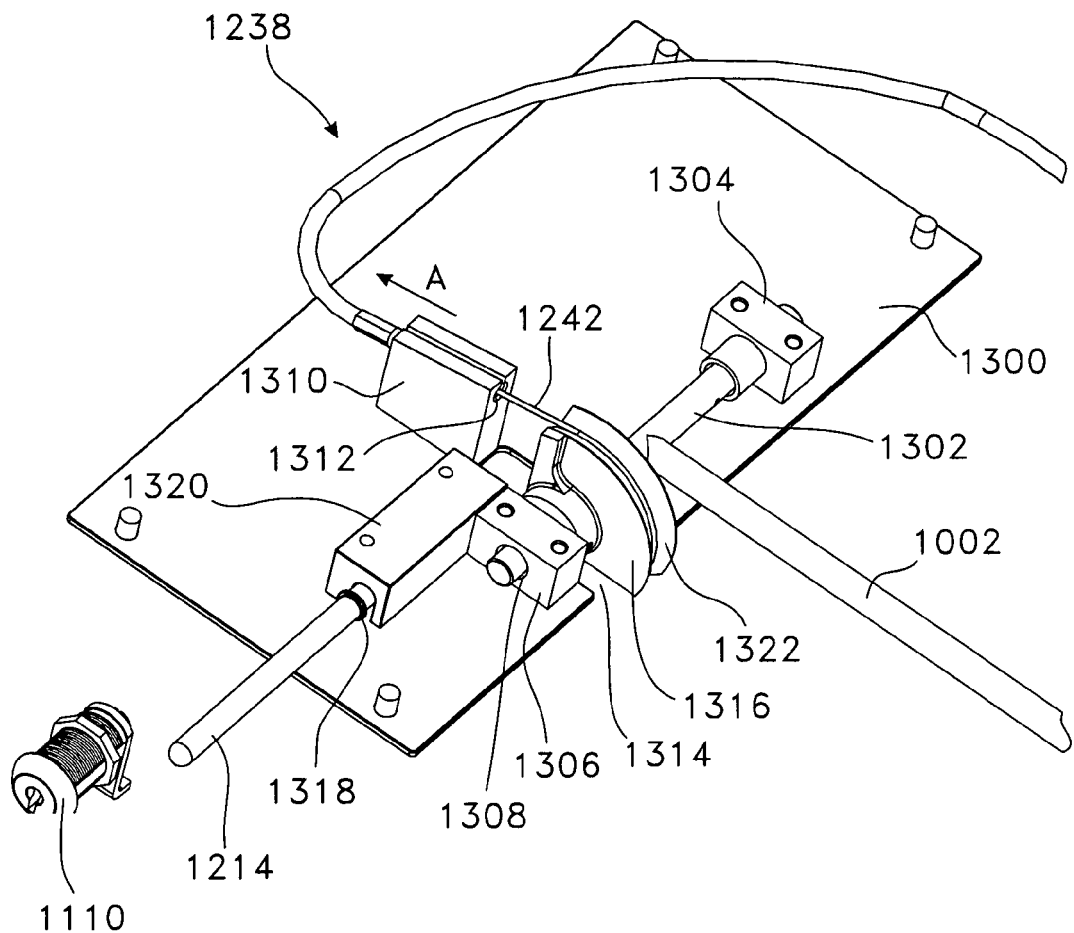
FIG. 16C is an enlarged perspective view of the upper portion of the container system shown in FIG. 16A.
Figure 16D:
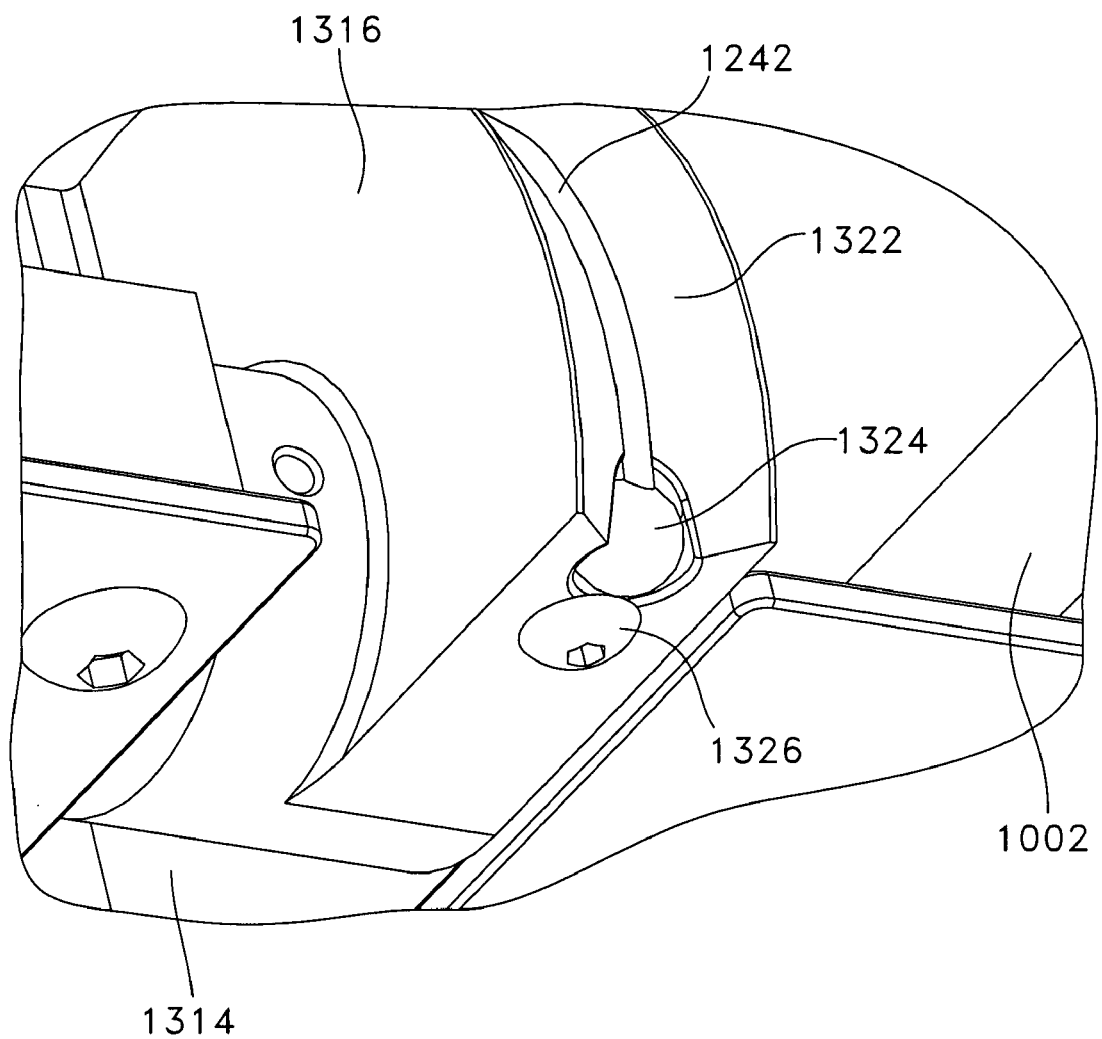
FIG. 16D is a further enlarged perspective view of the upper portion of the container system shown in FIG. 16A.

As shown in FIG. 16D, the core 1242 of the flexible member terminates at a ball 1324 that is engaged within a recess formed in or adjacent the grooved surface of the pulley 1316. A fastener such as a screw 1326 retains the ball 1324 in place to prevent its removal, thereby maintaining the connection or termination of the core 1242 at the pulley 1316.

Although this invention has been described with reference to particular embodiments selected for illustration in the Figures, it will be appreciated that many variations and modifications can be made to the system 10 and the components thereof without departing from the spirit or the scope of this invention. The ornamental appearance of the body 105 and hood 104 of the carrier 100 can be modified into a large number of possible configurations. Also, the materials used to form the hood 104 and body 105, as well as the manufacturing techniques used to form those components, can also be modified. Although the body 105 and hood 104 are preferably formed from plastic using a rotational molding technique, metallic and other materials can be used and the body and hood can be formed using other manufacturing techniques.

It will also be appreciated that the mechanism used to couple the lever 114 to the arm 202 can be varied within the scope of this invention. For example, the flexible cable can be replaced with a rigid linkage. Also, the location and form of the lever 114 can be changed. While the lever 114 preferably takes the form of a foot pedal located near the base of the carrier 100, the lever can also be a hand-operated lever located towards an upper portion of the carrier 100.

It will further be appreciated that the mechanism used to translate movement from the food pedal or other actuation device to the arm component 1002 can be varied within the scope of this invention. A wide variety of linkages, couplings, or other mechanisms are optionally employed to urge movement of an arm component with respect to the remainder of a carrier.

Additional variations can also be made within the scope of this invention, which is defined separately in the following claims:

What is claimed:

1. A carrier for holding a container having a door mounted for reciprocation between opened and closed positions, said carrier comprising:
    a body portion at least partially defining a cavity to receive a container;
    an upper portion coupled to the body portion and extendable over at least a portion of the container;
    an arm coupled to said upper portion for pivotal movement with respect to said upper portion, said arm engagable with said door of said container, and pivotal movement of said arm capable of reciprocating said door of said container between said opened and closed positions; and
    a spring coupled to the upper portion and to the arm, wherein said arm is pivotable against a bias of said spring.

2. The carrier of claim 1, wherein said arm is biased by said spring to urge said door toward said closed position.

3. A carrier for holding a container having a door mounted for reciprocation between opened and closed positions, said carrier comprising:
    a body portion at least partially defining a cavity to receive a container;
    an upper portion coupled to the body portion for movement between a first position, wherein the upper portion is oriented to facilitate insertion and removal of the container, and a second position, wherein the upper portion is oriented to inhibit insertion and removal of the container;
    an arm coupled to said upper portion for pivotal movement with respect to said upper portion, said arm engagable with said door of the container, and pivotal movement of said arm capable of reciprocating said door of the container between said opened and closed positions, wherein the arm is coupled to said upper portion for pivotal movement about an arm pivot axis that is oriented substantially parallel to a door pivot axis; and
    a flexible member coupled to said arm, wherein the arm is reciprocally pivoted about the arm pivot axis by a tension applied to the flexible member, wherein said flexible member comprises a cable.

4. A carrier for holding a container having a door mounted for reciprocation between opened and closed positions, said carrier comprising:
    a body portion at least partially defining a cavity to receive a container;
    an upper portion coupled to the body portion and extendable over at least a portion of the container;
    an arm coupled to said upper portion for pivotal movement with respect to said upper portion, said arm engagable with said door of said container, and said pivotal movement of said arm capable of reciprocating said door of said container between said opened and closed positions, wherein the arm is coupled to said upper portion for pivotal movement about an arm pivot axis that is oriented substantially parallel to a door pivot axis;
    a flexible member coupled to said arm, wherein the arm is reciprocally pivoted about the arm pivot axis by tension applied to the flexible member; and
    a lever pivotally coupled to said body portion, wherein tension is applied to said flexible member by actuation of said lever.

5. A carrier for holding a container having a door mounted for reciprocation between opened and closed positions, said carrier comprising:
    a body portion at least partially defining a cavity to receive a container;

an upper portion coupled to the body portion and extendable over at least a portion of the container;

an arm coupled to said upper portion for pivotal movement with respect to said upper portion, said arm engagable with said door of said container, and said pivotal movement of said arm capable of reciprocating said door of said container between said opened and closed positions, wherein the arm is coupled to said upper portion for pivotal movement about an arm pivot axis that is oriented substantially parallel to a door pivot axis;

a flexible member coupled to said arm, wherein the arm is reciprocally pivoted about the arm pivot axis by a tension applied to the flexible member;

a lever pivotally coupled to said body portion, wherein tension is applied to said flexible member by actuation of said lever; and a locking bracket coupled to the body portion for reciprocation between a locked position preventing said lever from pivoting to open said door of said container and an unlocked position in which said lever may pivot to open said door of said container.

6. A carrier for holding a container having a door mounted for reciprocation between opened and closed positions, said carrier comprising:

a body portion at least partially defining a cavity to receive a container, the body portion being configured to support said container;

an upper portion coupled to the body portion and extendable over at least a portion of the container;

an arm coupled to said upper portion for pivotal movement with respect to said upper portion, said arm engagable with said door of said container, and said pivotal movement of said arm capable of reciprocating said door of said container between said opened and closed positions;

a pivoting portion pivotally coupled to said body portion to pivot between a closed position wherein said pivoting portion restrains said container within said body portion and an open position wherein said container may be removed from said body portion; and a lock positioned for locking said pivoting portion in said closed position with respect to said body portion.

7. The carrier of claim 6, wherein said lock is lockable and unlockable by use of a key.

8. The carrier of claim 6, wherein said arm extends from said pivoting portion for reciprocation with respect to said pivoting portion.

9. A carrier for holding a container having a door mounted for reciprocation between opened and closed positions, said carrier comprising:

a body portion at least partially defining a cavity to receive a container;

an upper portion coupled to the body portion and extendable over at least a portion of the container;

an arm coupled to said upper portion for pivotal movement with respect to said upper portion, said arm engagable with said door of said container, and said pivotal movement of said arm capable of reciprocating said door of said container between said opened and closed positions, wherein said arm is coupled to said upper portion for pivotal movement about an arm pivot axis that is oriented substantially parallel to a door pivot axis; and a biasing member coupled to said arm, wherein said arm is reciprocally pivoted about said arm pivot axis against a bias of said biasing member.

10. The carrier of claim 9, wherein said biasing member comprises a spring.

11. A carrier for holding a container having a door mounted for reciprocation between opened and closed positions, said carrier comprising:

a body portion at least partially defining a cavity to receive a container, the body portion being configured to support said container;

an upper portion movably coupled to the body portion and extendable over at least a portion of the container;

an arm coupled to said upper portion for pivotal movement with respect to said upper portion, said arm engagable with said door of said container, and said pivotal movement of said arm capable of reciprocating said door of said container between said opened and closed positions;

a pivoting portion pivotally coupled to said body portion to pivot between a closed position wherein said pivoting portion restrains said container within said body portion and an open position wherein said container may be removed from said body portion; and a biasing member coupled to said arm and to said pivoting portion, wherein said arm is reciprocally pivoted about said arm pivot axis against a bias of said biasing member.

12. A carrier for holding a container having a door mounted for reciprocation between opened and closed positions, said carrier comprising:

a body portion at least partially defining a cavity to receive a container;

an upper portion coupled to the body portion;

an arm coupled to said upper portion for pivotal movement with respect to said upper portion, said arm engagable with said door of said container, and said pivotal movement of said arm capable of reciprocating said door of said container between said opened and closed positions; and a locking member for selectively resisting said pivotal movement of said arm.

13. A carrier for receiving a container having a door mounted for reciprocation between opened and closed positions, said carrier having:

a body portion;

an arm coupled for reciprocal movement with respect to said body portion, said arm having a first portion coupled to the body portion and a second portion pivotally coupled by a pivot linkage to the first portion, the second portion being configured and dimensioned to selectively engage the door of the container;

an upper portion coupled to the body portion and rotatable to a first position and a second position, said upper portion covering at least a portion of the container, thereby inhibiting removal of the container when the upper portion is in the first position and allowing removal of the container when the upper portion is in the second position; and a keyed lock for locking said upper portion in said first position with respect to said body portion.

14. The carrier of claim 13, said first portion of said arm comprising an elongated segment.

15. The carrier of claim 14, said elongated segment being formed from a rod.

16. A carrier for receiving a container having a door mounted for reciprocation between opened and closed positions, said carrier having:

a body portion; and an arm coupled for reciprocal movement with respect to said body portion, said arm having a first portion coupled to the body portion and a second portion pivotally coupled by a pivot linkage to the first portion, said second portion of said arm comprising a hook shaped to engage said door, wherein said hook is shaped to releasably engage an edge surface of said door.

17. The carrier of claim 16, wherein the arm is coupled to said body portion such that the arm is automatically movable via gravity to cause engagement of the second portion with the door.

18. The carrier of claim 16, wherein the second portion of the arm is configured and dimensioned for manual manipulation to facilitate engagement with and disengagement from the door.

19. A carrier for receiving a container having a door mounted for reciprocation between opened and closed positions, said carrier having:
  a body portion; and
  an arm coupled for reciprocal movement with respect to said body portion, said arm having a first portion coupled to the body portion and a second portion pivotally coupled by a pivot linkage to the first portion, the second portion being configured and dimensioned to selectively engage the door of the container, wherein said second portion of said arm comprises a contact surface positioned to facilitate manual pivoting of said second portion with respect to said first portion of said arm, said contact surface being defined by a recess formed in said second portion.

20. The carrier of claim 19, said second portion of said arm having a center of gravity positioned forward of said pivot linkage.

21. A carrier for holding a container having a door mounted for reciprocation between opened and closed positions, said carrier having:
  a body portion defining a cavity for receiving the container, said body portion having a wall portion that is substantially hollow;
  an arm coupled for reciprocal movement with respect to said body portion; and
  a flexible member coupled to said arm to facilitate said reciprocal movement of said arm, said flexible member extending through said substantially hollow wall portion of said body portion,
  wherein said arm is adapted to engage the door of the container and said reciprocal movement of said arm is adapted to reciprocate the door of the container between the opened and closed positions.

22. The carrier of claim 21, wherein said body portion is formed from rotationally-molded plastic.

23. The carrier of claim 21, further comprising an upper portion coupled for movement with respect to said body portion.

24. The carrier of claim 21, wherein said flexible member comprises a sheath and a core extending within said sheath.

25. The carrier of claim 24, wherein said core is formed from a cable.

26. The carrier of claim 21, said arm of said carrier being mounted for pivotal reciprocation about an arm pivot axis, said carrier further comprising a pivot member coupled to said arm and mounted for rotation about said arm pivot axis.

27. The carrier of claim 26, said flexible member being coupled to said pivot member.

28. The carrier of claim 21, further comprising a grooved member coupled to said pivot member, said flexible member being coupled to said grooved member.

29. The carrier of claim 28, said grooved member comprising a pulley.

30. The carrier of claim 21, said arm being mounted for reciprocation along a path corresponding to a longitudinal axis of said arm.

* * * * *